(12) United States Patent
Kamee et al.

(10) Patent No.: US 10,314,462 B2
(45) Date of Patent: Jun. 11, 2019

(54) OBSERVATION APPARATUS

(71) Applicant: OLYMPUS CORPORATION, Tokyo (JP)

(72) Inventors: Hiroyuki Kamee, Koganei (JP); Masahiro Nishio, Hachioji (JP); Takeshi Ito, Hino (JP); Eiji Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 14/979,791

(22) Filed: Dec. 28, 2015

(65) Prior Publication Data

US 2016/0106299 A1    Apr. 21, 2016

Related U.S. Application Data

(63) Continuation of application No. PCT/JP2014/066155, filed on Jun. 18, 2014.

(30) Foreign Application Priority Data

Jun. 27, 2013   (JP) .................................. 2013-135489

(51) Int. Cl.
*H04N 5/235*   (2006.01)
*A61B 1/00*   (2006.01)
(Continued)

(52) U.S. Cl.
CPC ...... *A61B 1/00006* (2013.01); *A61B 1/00045* (2013.01); *A61B 1/04* (2013.01);
(Continued)

(58) Field of Classification Search
CPC ..... A61B 1/00006; A61B 1/05; A61B 1/0638; A61B 1/00045; A61B 1/04; H04N 5/2351;
(Continued)

(56) References Cited

U.S. PATENT DOCUMENTS

2006/0103738 A1*   5/2006   Sano ..................... H04N 5/2256
                                                      348/222.1
2006/0147189 A1*   7/2006   Yogesan .................. A61B 3/12
                                                      396/18
(Continued)

FOREIGN PATENT DOCUMENTS

CN          104981199 A       10/2015
EP          2 465 432 A1       6/2012
(Continued)

OTHER PUBLICATIONS

Chinese Office Action dated Feb. 13, 2017 in Chinese Patent Application No. 201480036441.5.
(Continued)

*Primary Examiner* — Zaihan Jiang
(74) *Attorney, Agent, or Firm* — Scully, Scott, Murphy & Presser, P.C.

(57) ABSTRACT

An observation apparatus includes an imager, a light source unit, an image processor and a light intensity adjusting section. The imager includes types of elements which generate a first signal when the elements receive light included in a sensitivity region. The light source unit includes light sources to emit narrow spectrum light, wavelengths of the light being different from one another and being set so that at least one of the wavelengths is included in each of the sensitivity regions. The image processor generates display data indicating a color image on the basis of the image data. The light intensity adjusting section separately adjusts respective light intensity of the light sources.

12 Claims, 9 Drawing Sheets

(51) Int. Cl.
    *A61B 1/04*     (2006.01)
    *A61B 1/06*     (2006.01)
    *G02B 23/24*     (2006.01)
    *A61B 1/05*     (2006.01)

(52) U.S. Cl.
CPC .............. *A61B 1/05* (2013.01); *A61B 1/0638* (2013.01); *G02B 23/2423* (2013.01); *G02B 23/2469* (2013.01); *H04N 5/2351* (2013.01); *H04N 5/2354* (2013.01); *A61B 1/00009* (2013.01)

(58) Field of Classification Search
CPC .............. H04N 5/2354; G02B 23/2423; G02B 23/2469
USPC .......................................................... 348/67
See application file for complete search history.

(56) References Cited

U.S. PATENT DOCUMENTS

| | | | | |
|---|---|---|---|---|
| 2010/0079503 | A1* | 4/2010 | Ramanath | G09G 3/3413 345/690 |
| 2011/0058237 | A1* | 3/2011 | Mikami | H04N 1/40056 358/509 |
| 2011/0149306 | A1* | 6/2011 | Kim | H04N 1/02815 358/1.6 |
| 2011/0237880 | A1* | 9/2011 | Hamel | A61B 1/00009 600/104 |
| 2012/0078046 | A1* | 3/2012 | Sasaki | A61B 1/00009 600/109 |
| 2012/0154567 | A1 | 6/2012 | Yamaguchi et al. | |
| 2012/0248561 | A1* | 10/2012 | Hakko | G02B 3/0043 257/432 |
| 2013/0041218 | A1 | 2/2013 | Iida et al. | |
| 2013/0167389 | A1* | 7/2013 | Christoph | G01B 21/045 33/503 |
| 2013/0329163 | A1* | 12/2013 | Wu | G02F 1/133603 349/64 |
| 2014/0159587 | A1* | 6/2014 | Sezan | G09G 3/3466 315/152 |
| 2014/0300780 | A1* | 10/2014 | Kim | H04N 5/2354 348/234 |
| 2015/0335232 | A1 | 11/2015 | Ito et al. | |

FOREIGN PATENT DOCUMENTS

| | | |
|---|---|---|
| EP | 2 556 790 A1 | 2/2013 |
| EP | 2 954 836 A1 | 12/2015 |
| JP | 10-286235 A | 10/1998 |
| JP | 2012-125501 A | 7/2012 |
| JP | 2013-34753 A | 2/2013 |
| JP | 2013-42855 A | 3/2013 |

OTHER PUBLICATIONS

English translation of International Preliminary Report on Patentability dated Jan. 7, 2016 together with the Written Opinion received in related International Application No. PCT/JP2014/066155.
Japanese Office Action dated Sep. 19, 2017 in Japanese Patent Application No. 2013-135489.
Japanese Office Action dated May 16, 2017 in Japanese Patent Application No. 2013-135489.
Extended Supplementary European Search Report dated Jan. 18, 2017 in related European Patent Application No. 14 81 7097.0.
Japanese Office Action dated Jan. 10, 2017 in related Japanese Patent Application No. 2013-135489.
Neumann, A., et al., "Four-color laser white illuminant demonstrating high color-rendering quality", Optics Express A982, Jul. 2, 2011, vol. 19, No. S4.
International Search Report dated Aug. 5, 2014 issued in PCT/JP2014/066155.

* cited by examiner

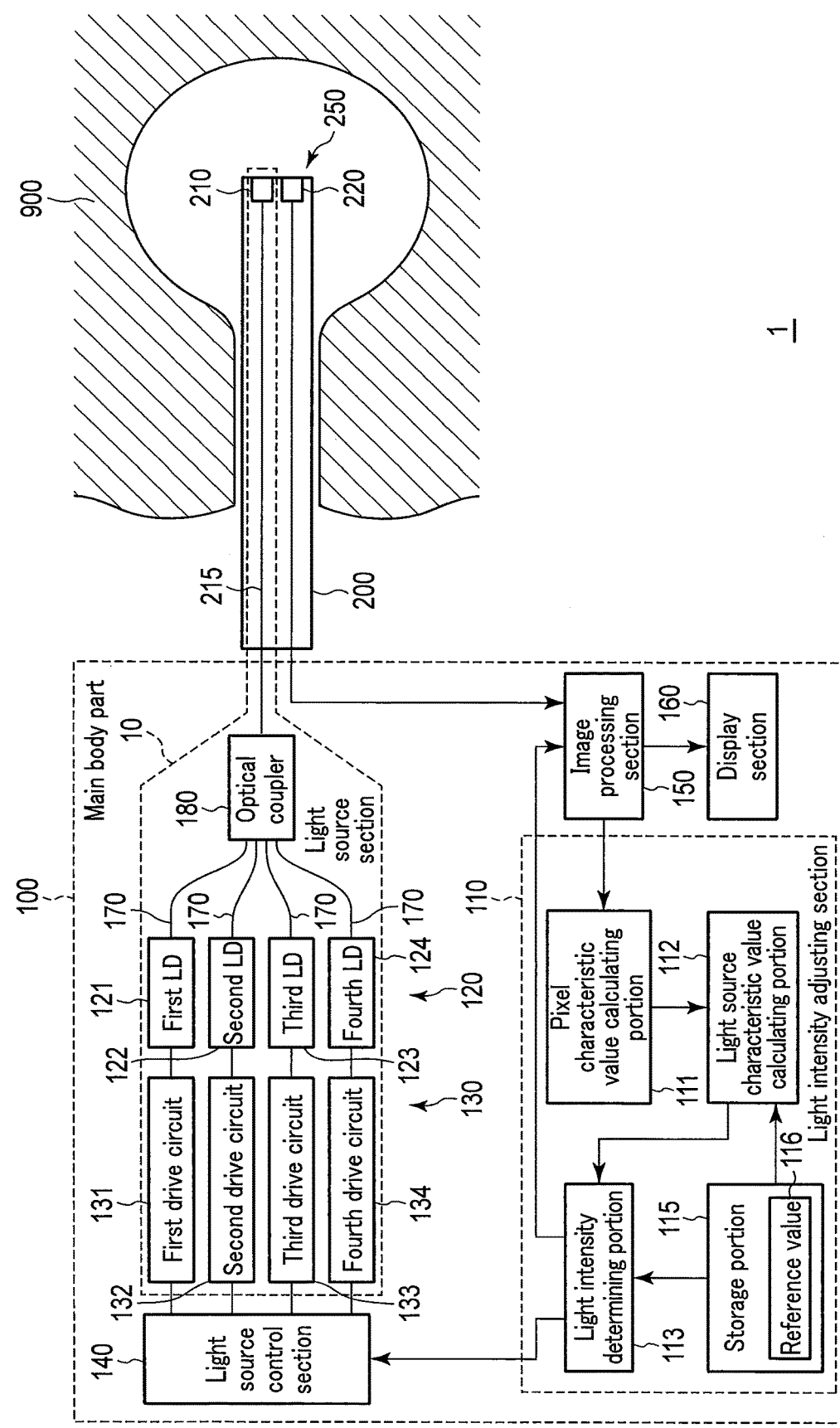
F I G. 1

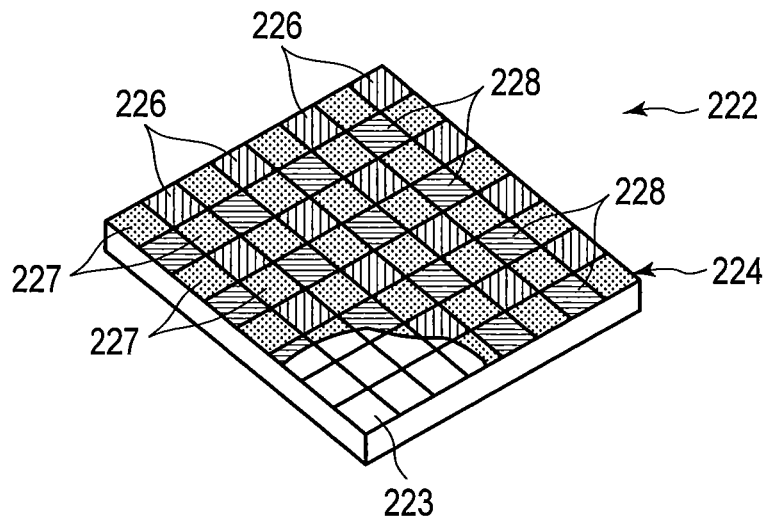
F I G. 2
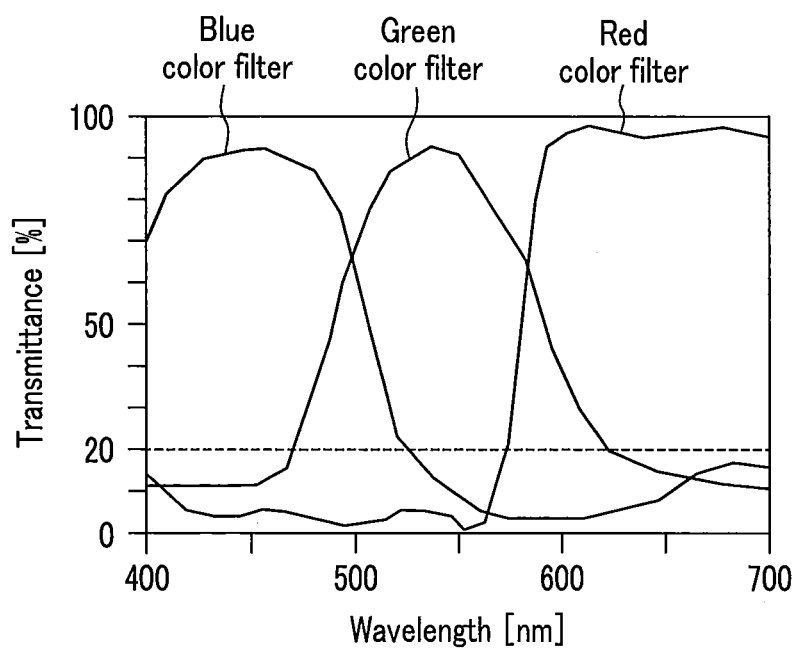
F I G. 3

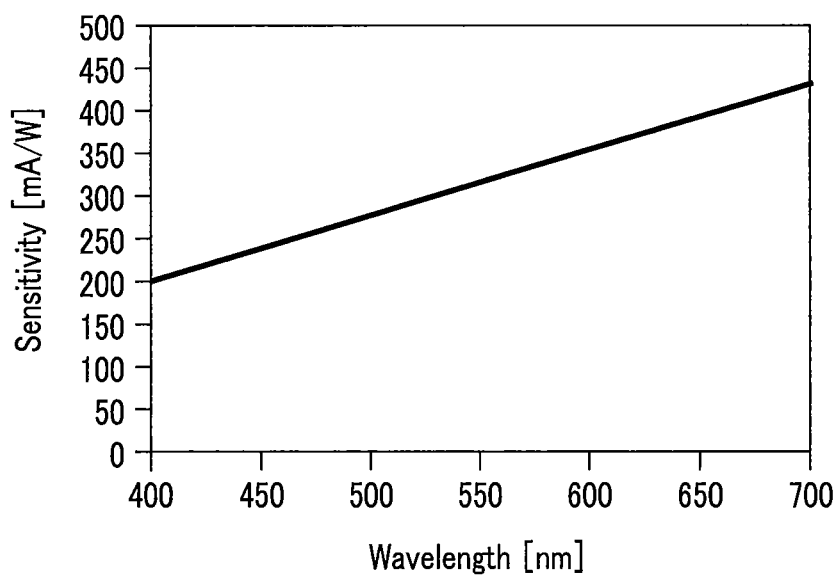
F I G. 4
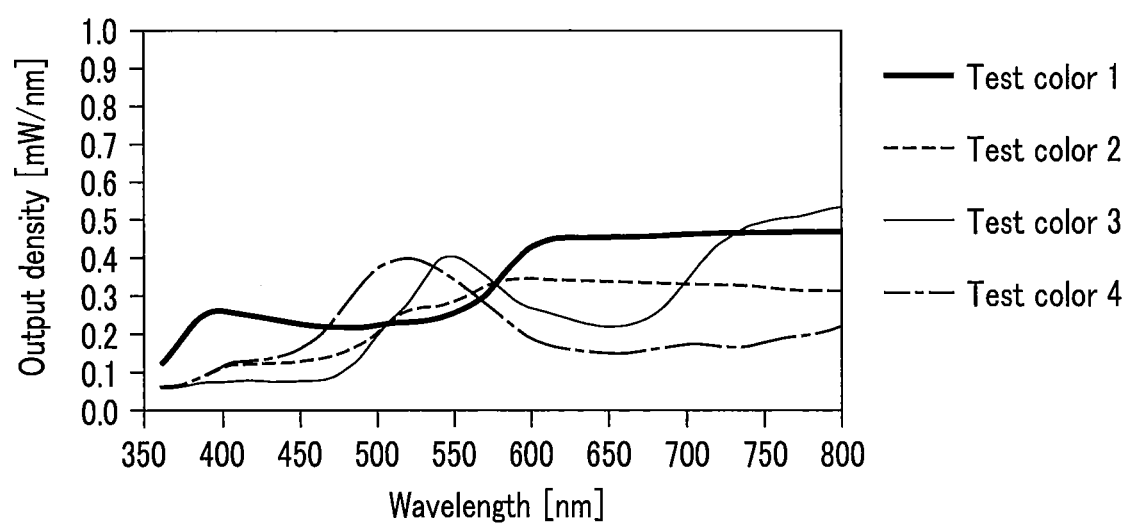
F I G. 5A

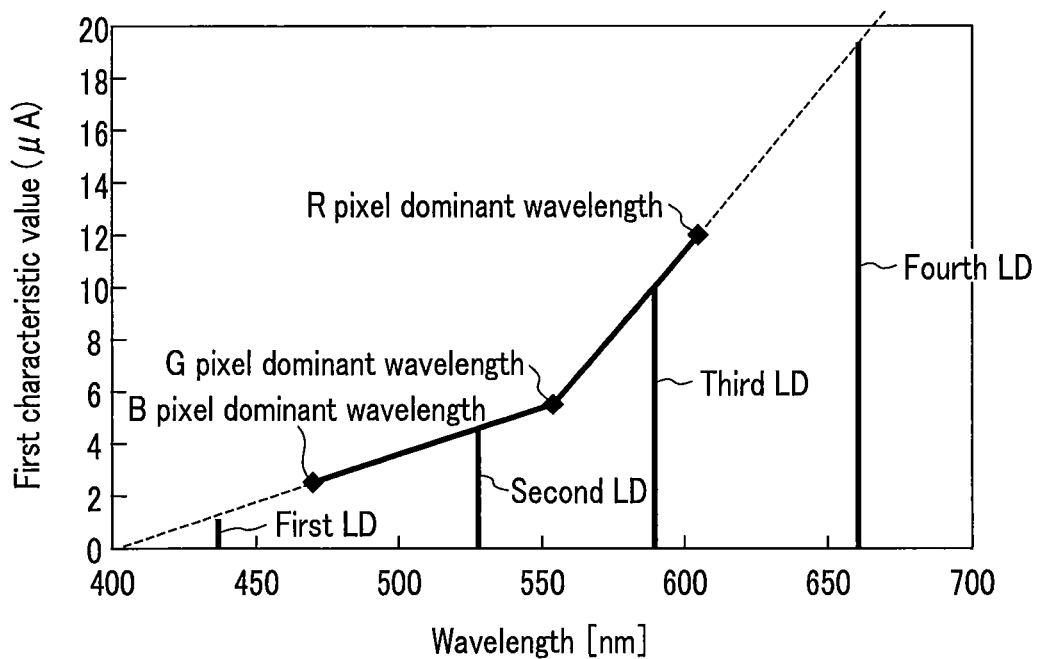
F I G. 11
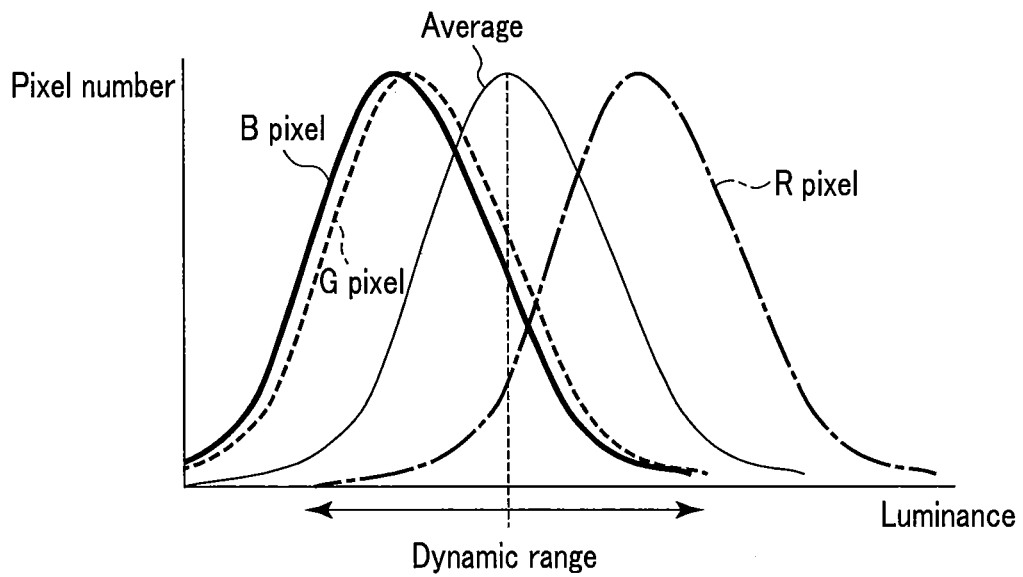
F I G. 12

| R/G  B/G | --- | 1~2 | 2~3 | --- |
|---|---|---|---|---|
| --- | | | | |
| 1/3~1/2 | | First object L1=A time(s) L2=B time(s) L3=C time(s) L4=D time(s) | Second object L1=E time(s) L2=F time(s) L3=G time(s) L4=H time(s) | |
| 1/2~1 | | Third object L1=I time(s) L2=J time(s) L3=K time(s) L4=L time(s) | Fourth object L1=M time(s) L2=N time(s) L3=O time(s) L4=P time(s) | |
| --- | | | | |

FIG. 14

OBSERVATION APPARATUS

CROSS-REFERENCE TO RELATED APPLICATIONS

This application is a Continuation application of PCT Application No. PCT/JP2014/066155, filed Jun. 18, 2014 and based upon and claiming the benefit of priority from prior Japanese Patent Application No. 2013-135489, filed Jun. 27, 2013, the entire contents of all of which are incorporated herein by reference.

BACKGROUND OF THE INVENTION

1. Field of the Invention

The present invention relates to an observation apparatus.

2. Description of the Related Art

As a laser light source, a gas light source has heretofore been used, whereas a solid light source has advantages such as low power consumption, high connection efficiency, small size, and high speed switchability. Technical innovations concerning such a solid light source have been remarkable. A so-called fiber light source is known in which such a miniaturized solid light source and an optical fiber are combined. The fiber light source is suitable to illuminate the inside of a narrow structure. Therefore, application to an endoscope or the like has also been advanced.

For example, in a publication of Jpn. Pat. Appln. KOKAI Publication No. H10-286235, there is disclosed an example where a light source device in which a laser light source of three colors of red (R), green (G) and blue (B), an optical fiber and a diffusion plate are combined is mounted in an endoscope. The optical fiber guides light from the laser light source at a high efficiency, and hence according to this combination of the laser light source and the optical fiber, the light source device having a high efficiency and brightness can be realized. In the light source device according to the publication of Jpn. Pat. Appln. KOKAI Publication No. H10-286235, there are used an He—Cd laser light source as a laser light source of three primary colors (a white color) which simultaneously emits blue laser light of a wavelength of 441.6 nm, green laser light of a wavelength of 537.8 nm and red laser light of a wavelength of 636.0 nm, and an He—Ne laser light source which emits red laser light of a wavelength of 632.8 nm. The laser light emitted from these light sources are guided to a distal end of the endoscope through the optical fiber, to irradiate a living body that is an illumination object via the diffusion plate and an illuminance distribution adjusting filter.

When diffused laser light is generally used as illuminating light, information of the light of the wavelength that is not included in the laser light is missing. That is, for example, in a case where the laser light of the wavelength of 636.0 nm is used as the red color, it is known that color reproducibility of the red color worsens when a reflectance of an observation object to the light of the wavelength of 636.0 nm in the red color is noticeably different from a reflectance of the observation object to light of a wavelength other than the above wavelength. For example, when there is observed an object that hardly reflects light of a wavelength in the vicinity of 636.0 nm but reflects another light of a red region better, the object actually appears to be red, but when the object is illuminated with the red laser light of the wavelength of 636.0 nm, the object might appear to be dark. In the abovementioned publication of Jpn. Pat. Appln. KOKAI Publication No. H10-286235, for the purpose of improving the color reproducibility of the red color, a red laser light source of the wavelength of 632.8 nm is used in addition to the red laser light source of the wavelength of 636.0 nm. However, a difference in wavelength of the laser light to be emitted from these light sources is merely 3.2 nm. As the wavelength difference is small, little improvement in the color reproducibility can be expected.

In the abovementioned technology according to the publication of Jpn. Pat. Appln. KOKAI Publication No. H10-286235, the mixed laser light is white.

BRIEF SUMMARY OF THE INVENTION

According to an aspect of the invention, an observation apparatus includes an imager that includes types of elements each of which performs photoelectric conversion to generate a first signal when receiving light included in a sensitivity region that is a predetermined wavelength region and in which the sensitivity regions are different from one another, the imager generating image data including the first signal based on an object image; a light source unit which includes light sources to emit narrow spectrum light, wavelengths of the narrow spectrum light emitted by each of the light sources being different from one another, and the wavelengths of the narrow spectrum light being set so that at least one of the wavelengths of the narrow spectrum light is included in each of the sensitivity regions of the types of the elements included in the imager; an image processor comprising hardware, wherein the processor is configured to generate display data indicating a color image on the basis of the image data; and a light intensity adjusting section that separately adjusts each light intensity of the light sources so that a color reproducibility of the color image heightens.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram schematically showing a configuration example of an observation apparatus according to a first embodiment;

FIG. 2 is a view schematically showing a configuration example of an image sensor;

FIG. 3 is a diagram showing one example of optical characteristics of filters;

FIG. 4 is a diagram showing one example of a relation between a wavelength of entering light and a sensitivity of photoelectric conversion in a photoelectric converting element;

FIG. 5A is a diagram showing reflection spectrums of standard test colors;

FIG. 11 is a diagram showing one example of a relation between a first characteristic value and each dominant wavelength;

FIG. 12 is a histogram showing luminance values of light entering into an R pixel, a G pixel and a B pixel when an object that exhibits a red color is imaged and frequencies of the values;

FIG. 14 is a diagram schematically showing one example of a light intensity determining table.

DETAILED DESCRIPTION OF THE INVENTION

First Embodiment

Figure 5B:
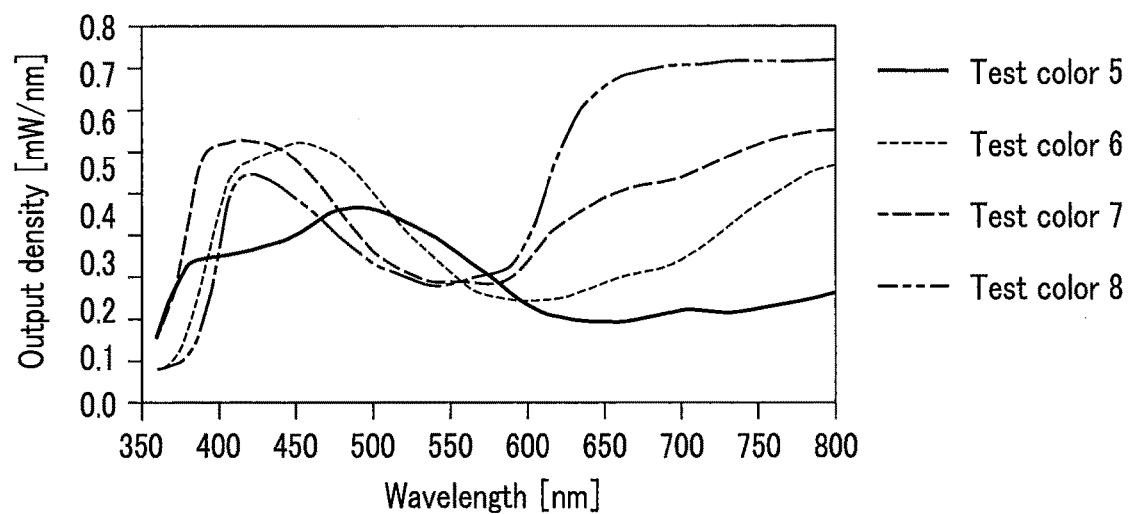
FIG. 5B is a diagram showing reflection spectrums of standard test colors.

A first embodiment of the present invention will be described with reference to the drawings. FIG. 1 schematically shows a configuration example of an observation apparatus 1 according to the present embodiment. As show in FIG. 1, the observation apparatus 1 comprises a main body part 100 and an inserting part 200 to be inserted in a dark place where there is no light from outside. The observation apparatus 1 is an apparatus that images an object while emitting illuminating light from a distal end of the inserting part 200, for dark part observation.

The inserting part 200 has an elongated shape, and its one end is connected to the main body part 100. The one end of this inserting part on a side connected to the main body part 100 is referred to as a proximal end side, and the other end is referred to as a distal end side. At a distal end 250 of the inserting part 200, a light emitting section 210 and an imaging section (imager) 220 are disposed. The light emitting section 210 is connected to one end of an optical fiber 215. The other end of the optical fiber 215 is connected to the main body part 100. The optical fiber 215 guides the illuminating light from the main body part 100 to the light emitting section 210. The illuminating light guided by the optical fiber 215 is emitted from the light emitting section 210.

The inserting part 200 is shaped to be easy to be inserted into an inner space of an observation object. In other words, the inserting part 200 is shaped to be easy to illuminate the inner space of the observation object having a narrow inlet that is hard to be illuminated by a general light source device. For example, as shown in FIG. 1, it is considered that an inner space of an observation object 900 is a slightly extending space that is present on a distal side of the narrow inlet, or the like. It is hard for indoor illumination or external light such as sunlight to penetrate into this space. In particular, when the inserting part 200 is inserted, the narrow inlet is further narrowed by the inserting part, and hence the external light hardly penetrates inside. That is, the illuminating light in the inner space is mostly the light emitted out from the light emitting section 210. In a situation where the observation apparatus 1 is used, the external light is almost negligible as compared with the light emitted out from the light emitting section 210.

The imaging section 220 includes an image sensor. The image sensor generates an electric charge in accordance with a quantity of the light to be received, by photoelectric conversion. The imaging section 220 uses the image sensor to image the object illuminated with the light emitted out from the light emitting section 210, and converts the reflected light into an electric signal. The imaging section 220 outputs this electric signal as image data to the main body part 100.

As shown in FIG. 2, in an image sensor 222 included in the imaging section 220, pixels 223 are disposed. In the image sensor 222, a color filter 224 is patterned. The color filter 224 includes a region having a red color filter, a region having a green color filter and a region having a blue color filter corresponding to the pixels 223. These pixels and filters are arranged in accordance with, for example, a Bayer array. The pixels in which the red color filter is formed are referred to as R pixels 226, the pixels in which the green color filter is formed are referred to as G pixels 227, and the pixels in which the blue color filter is formed are referred to as B pixels 228.

FIG. 3 shows light transmission characteristics of the color filter 224, i.e., a relation of a transmittance to a wavelength. As shown in FIG. 3, the blue color filter mainly transmits the light of a wavelength of the order of 400 nm, the green color filter mainly transmits the light of a wavelength of the order of 500 nm, and the red color filter mainly transmits the light of a wavelength of 600 nm or more.

Each of the pixels 223 of the image sensor 222 generates the electric signal by the photoelectric conversion. The R pixel 226 mainly converts intensity of red light into the electric signal, the G pixel 227 mainly converts intensity of green light into the electric signal, and the B pixel 228 mainly converts intensity of blue light into the electric signal. Each of the electric signals of separate wavelength regions which are generated in these respective pixels is referred to as a first signal. The image sensor 222 outputs the image data including information on a large number of the first signals as a whole.

FIG. 4 shows a relation between a wavelength of entering light and a sensitivity of the photoelectric conversion pertaining to a photoelectric converting element for use in the image sensor 222. As shown in FIG. 4, the sensitivity concerning the photoelectric conversion of the image sensor 222 varies in accordance with the wavelength. Additionally, in the image sensor 222, a proper light quantity range is present in which a signal corresponding to the light quantity can be output. When the light quantity is smaller than the proper light quantity range, the electric signal based on the received light is buried in noise, and an output corresponding to the light quantity cannot be obtained. On the other hand, when the light quantity is larger than the proper light quantity range, the image sensor 222 is put in a saturated state where a given amount of the electric charge or more cannot be accumulated, and cannot output the electric signal corresponding to the light quantity. A range in which the image sensor 222 can output the electric signal corresponding to the light quantity is referred to as a dynamic range of the image sensor 222.

A light source for use in the observation apparatus 1 preferably includes laser light sources each of which emit light of different wavelengths. It is assumed that the observation apparatus 1 is for use in observation of the inside of a closed space having a narrow inlet, and hence a diameter of the inserting part 200 is required to be decreased. The laser light source has a small light emitting point, and laser light to be emitted has a high rectilinearity, and hence the laser light is easy to be introduced into a small-diameter optical member such as the optical fiber. In consequence, the use of the laser light source is advantageous in decreasing the diameter of the inserting part 200.

Additionally, it is known that even as to a narrow spectrum light such as the laser light, a sufficient performance (color rendering properties) of the illuminating light can be obtained by light obtained by mixing light having different wavelengths included in a visible light region (see, e.g., A. Neumann et al., Opt. Exp., 19, S4, A982 (Jul. 4, 2011), the entire contents of which is incorporated herein by reference). Furthermore, image information obtained by one type of narrow spectrum light might include information on a substance having peculiar reflecting properties in its wavelength. Therefore, the laser light that is the narrow spectrum light also has the advantage that it is possible to obtain information that cannot be obtained by observation with usual white light.

A semiconductor laser light source is a solid light source device in which a current is passed through a semiconductor element to emit the laser light. In general, as the semiconductor laser light source, a light source that emits light of various wavelengths of ultraviolet light to infrared light is put to practical use. The semiconductor laser light source has features such as a small size and power saving. For a high luminance, various wavelengths and the like, the semiconductor laser light source is often developed.

In the present embodiment, the types of pixels 223, e.g., the R pixels 226, the G pixels 227 and the B pixels 228 are disposed in the imaging section 220. For the R pixels 226, the G pixels 227 and the B pixels 228, the color filter 224 having such wavelength transmission characteristics as shown in FIG. 3 is disposed. When this wavelength sensitivity region does not include even one wavelength of the illuminating light, there is no point to the pixel 223 being there. Therefore, the wavelength sensitivity region of each of the pixels 223 preferably includes at least one wavelength of the illuminating light.

It is to be noted that in the present embodiment, the wavelength sensitivity region of each pixel 223 is defined as a wavelength region in which a transmittance of the corresponding color filter 224 is at least 20% or more. This is because it is technically difficult to set the transmittance of the color filter 224 to 0%, and the color filter 224 also has some transmitting properties also in a wavelength region other than the transmitting wavelength region. Needless to say, this definition can suitably be changed.

It is assumed that light reflection characteristics of the surface of the object are varied from a short wavelength to a long wavelength included in the visible light region. In consequence, the light source is requested to necessarily include one wavelength of each of at least three primary colors or each of a red region, a green to yellow region and a blue region that are called the three primary colors of light. Also in the above literature (Neumann et al.), four discretely set wavelengths of red (635 nm), yellow (589 nm), green (532 nm) and blue (457 nm) are selected as the wavelengths of the light source.

The color rendering properties are represented by, for example, a general color rendering index determined by International Commission on Illumination (CIE) or the Japanese Industrial Standards (JIS). The general color rendering index determined by CIE or JIS is an index indicating a degree of a color difference to be generated from a large number of test colors assumed to be present in the natural world, as compared with sunlight or black body radiating light. It is considered that the color reproducibility of the illuminating light whose general color rendering index is low is deteriorated not only in human eyesight but also in such an apparatus as in the present embodiment in which the image sensor 222 is used. That is, in the case where the general color rendering index is low, it is considered that an image to be acquired cannot sufficiently reproduce the original color of the object.

It is clarified by calculation that the color rendering properties do not heighten that much when the laser light source of three types of wavelengths corresponding to the three colors of the color filter 224 is used. When the number of the wavelengths of the light source increases, the general color rendering index usually increases. Also in the observation apparatus 1, it is preferable to use the illuminating light in which at least four types of narrow spectrum light are mixed.

A combination of the wavelengths of the narrow spectrum light for use as the light sources will be described. When a range in which the wavelength of the illuminating light is missing is broad in the visible light region, the image information of the object peculiar to the wavelength region undesirably cannot be obtained. With reference to eight types of reflection spectrums determined as standard test colors in CIE and JIS as shown in FIG. 5A and FIG. 5B, the reflection spectrum moderately changes in the whole region of 400 nm to 750 nm. Therefore, it is considered that the illuminating light does not have to be present in all the wavelength regions. In a case where the narrow spectrum light is used as the illuminating light, when the respective wavelengths of the illuminating light are excessively close to or apart from one another, specific wavelength region information is disadvantageously missing, and there is the fear that characteristic object color information cannot be reproduced. The general color rendering indexes standardized in CIE and JIS are calculated on the basis of spectrum information that is discrete at every 5 nm. Also from this fact, it is considered that the color rendering properties significantly improve when the adjacent wavelengths are at least 5 nm or more apart from each other. From the above description, it is desired that four types of laser light sources or more in which at least peak wavelengths are 5 nm or more apart from each other are used as the light sources of the observation apparatus 1. In the following description, when the wavelengths of the illuminating light are 5 nm or more apart from each other, this wavelength interval is referred to as a high color rendering property maintaining wavelength interval.

In addition, a state where a color image acquired by the observation apparatus 1 has high color reproducibility is called a high color reproducing state. It is to be noted that color image information indicates not only an information group conforming to a specific standard but also any information converted so that the information can appropriately visually be recognized with human eyes in a case where an image display device is connected to the observation apparatus 1.

As shown in FIG. 1, the main body part 100 is provided with a first semiconductor laser light source (LD) 121, a second semiconductor laser light source 122, a third semiconductor laser light source 123, and a fourth semiconductor laser light source 124 which are light sources of the illuminating light emitted out from the light emitting section 210. The wavelengths of the laser light to be emitted by these four semiconductor laser light sources are different from one another. It is to be noted that in the following description, the first semiconductor laser light source 121, the second semiconductor laser light source 122, the third semiconductor laser light source 123 and the fourth semiconductor laser light source 124 are referred to as a laser light source 120 as a whole. It is to be noted that, here, there is described an example where the semiconductor laser light source is used as the light source, but light sources which emit narrow spectrums, e.g., various laser light sources are usable in the light source.

Figure 6:
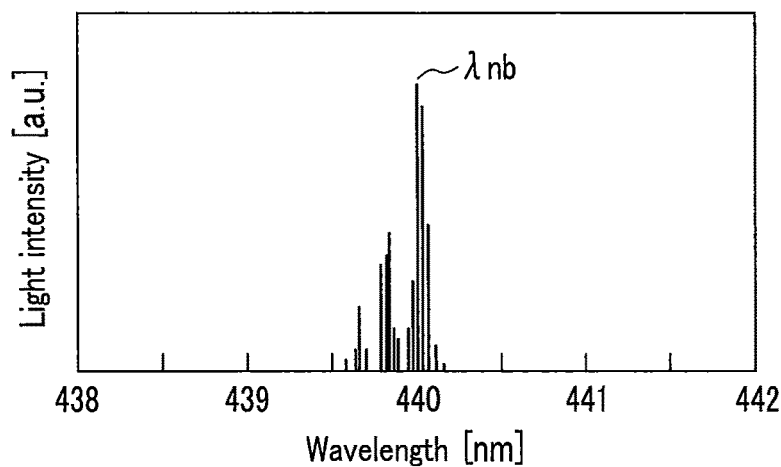
FIG. 6 is a diagram showing one example of an oscillation spectrum of a multimode semiconductor laser light source.

Each of the semiconductor laser light sources included in the laser light source 120 is a multimode laser light source. As shown in, for example, FIG. 6, the multimode semiconductor laser light source performs laser oscillation of wavelengths, but the wavelengths of the shortest one to the longest one are included in a wavelength region of about several nm. FIG. 6 shows one example of a light emission spectrum of the multimode semiconductor laser light source that emits the light at a wavelength of about 440 nm. This light emission spectrum has tens of line spectrum components, and a ratio or the number of line spectrums changes with an elapse of time. A width of the wavelength region of the light emission spectrum is about 1 nm. When multimode laser light having the spectrum described above is used as narrow band light, in the present embodiment, a peak wavelength λnb of the narrow band light is defined as the wavelength having the highest light intensity. In the present embodiment, a peak wavelength λnb1 of the first semiconductor laser light source 121 is 440 nm, and the light is blue. Similarly, a peak wavelength λnb2 of the second semiconductor laser light source 122 is 530 nm, and the light is green. A peak wavelength λnb3 of the third semiconductor laser light source 123 is 590 nm, and the light is orange. A peak wavelength λnb4 of the fourth semiconductor laser light source 124 is 640 nm, and the light is red.

In the present embodiment, the regions which do not include any laser light are defined as wavelength missing regions where the regions are a region between a laser light spectrum of the first semiconductor laser light source 121 and a laser light spectrum of the second semiconductor laser light source 122, a region between the laser light spectrum of the second semiconductor laser light source 122 and a laser light spectrum of the third semiconductor laser light source 123, and a region between the laser light spectrum of the third semiconductor laser light source 123 and a laser light spectrum of the fourth semiconductor laser light source 124. In the present embodiment, a width of 1 nm or less of a spectrum component in each laser light is in a negligible range as compared with a width of several tens of nm of the wavelength missing region. Therefore, it can be considered that a distance between the respective peak wavelengths is a width of the wavelength missing region.

As shown in FIG. 1, the main body part 100 is provided with a first drive circuit 131 that drives the first semiconductor laser light source 121, a second drive circuit 132 that drives the second semiconductor laser light source 122, a third drive circuit 133 that drives the third semiconductor laser light source 123, and a fourth drive circuit 134 that drives the fourth semiconductor laser light source 124. In the following description, the first drive circuit 131, the second drive circuit 132, the third drive circuit 133 and the fourth drive circuit 134 are referred to as a drive circuit 130 as a whole. The drive circuit 130 drives the laser light source 120, turns on or off the laser light source 120, and changes the light intensity. Furthermore, the main body part 100 is provided with a light source control section 140 which controls the operation of the drive circuit 130. The light source control section 140 controls the drive circuit 130 to drive the laser light source 120 on the basis of an output value determined by an after-mentioned light intensity adjusting section 110.

The main body part 100 is provided with an optical coupler 180. The laser light emitted out from the respective laser light source 120 is guided to the optical coupler 180 by optical fibers 170. The optical coupler 180 combines the respective guided laser light, and the combined light enters into the optical fiber 215 mentioned above. The illuminating light entering into the optical fiber 215 is guided to the light emitting section 210 of the distal end 250 by the optical fiber 215.

The light emitting section 210 is provided with a distal end optical member including, for example, a diffusing member to obtain the light guided by the optical fiber 215 as desirable illuminating light. From the light emitting section 210 in a direction of the object, the illuminating light in which four colors are mixed and laser light is diffused is emitted. Thus, the laser light source 120, the drive circuit 130, the optical fibers 170, the optical coupler 180, the optical fiber 215 and the light emitting section 210 form a light source section (light source unit) 10.

The main body part 100 further comprises the light intensity adjusting section 110 that determines a light intensity of the laser light to be emitted out from the laser light source 120, an image processing section 150 including image processor that processes the image data obtained by imaging the object with the imaging section 220, and a display section 160 including a display device such as a liquid crystal display element. The light intensity adjusting section 110 comprises a pixel characteristic value calculating portion 111, a light source characteristic value calculating portion 112, a light intensity determining portion 113, and a storage portion 115.

The pixel characteristic value calculating portion 111 acquires the image data from the image processing section 150. The pixel characteristic value calculating portion 111 calculates a first characteristic value on the basis of the acquired image data. Here, the first characteristic value is a characteristic value pertaining to the first signal. The first signal is an electric signal to be generated by each pixel pertaining to a predetermined wavelength region corresponding to a red color of the R pixel 226, a green color of the G pixel 227 and a blue color of the B pixel 228 in the imaging section 220 as described above. The pixel characteristic value calculating portion 111 transmits the first characteristic value to the light source characteristic value calculating portion 112.

The light source characteristic value calculating portion 112 calculates a second characteristic value on the basis of the first characteristic value acquired from the pixel characteristic value calculating portion 111. Here, the second characteristic value is a characteristic value of the light received by the imaging section 220 which is calculated every wavelength corresponding to the light source. The light source characteristic value calculating portion 112 transmits the second characteristic value to the light intensity determining portion 113. Thus, the light source characteristic value calculating portion 112 functions as a second characteristic value calculating portion that calculates the second characteristic value. Here, the second characteristic value indicates characteristics concerning output correction of each light source included in the laser light source 120. This output correction is correction concerning the light intensity, and the correction has an influence on the above intensity of the first signal.

The light intensity determining portion 113 calculates the output value, i.e., the intensity of the laser light to be emitted out from each light source in the laser light source 120, i.e., each of the first semiconductor laser light source 121, the second semiconductor laser light source 122, the third semiconductor laser light source 123 and the fourth semiconductor laser light source 124, on the basis of the second characteristic value acquired from the light source characteristic value calculating portion 112. The light intensity determining portion 113 transmits the calculated output value to the light source control section 140. In addition, the light intensity determining portion 113 transmits the output value to the image processing section 150.

The storage portion 115 stores a reference value 116 required for the abovementioned calculation. The storage portion 115 outputs the reference value 116 in accordance with a request from the light source characteristic value calculating portion 112 or the light intensity determining portion 113.

The light source control section 140 controls the drive circuit 130 to drive the laser light source 120 on the basis of the output value acquired from the light intensity determining portion 113. As a result, the laser light source 120 outputs the laser light corresponding to the output value determined by the light intensity adjusting section 110.

The image processing section 150 acquires the image data pertaining to an object image imaged by the imaging section 220. In addition, the image processing section 150 acquires the output value of the laser light source 120 from the light intensity determining portion 113. The image processing section 150 subjects the acquired image data to image processing. This image processing includes the correction pertaining to the output value of the laser light source 120 in addition to the usual image processing. That is, as to respective colors such as the blue color, the green color and the red color, the image processing section 150 performs the correction to decrease a value of the image data acquired by the imaging section 220 concerning a color having a high intensity of the light to be emitted out from the laser light source 120, and the image processing section performs the correction to increase a value of the image data acquired by the imaging section 220 concerning a color having a low intensity of the light to be emitted out from the laser light source 120. According to this correction, an image is generated in which the color of the object is represented when the object is irradiated with the white light as the illuminating light. The image processing section 150 generates display data having a format in which the color image can be displayed by the display section 160. The image processing section 150 outputs the display data to the display section 160, and the display section 160 displays the image of the object. In addition, the image processing section 150 outputs the image data acquired from the imaging section 220 to the pixel characteristic value calculating portion 111 without processing the data.

The light intensity adjusting section 110, the light source control section 140, and the image processing section 150 (image processor) include a hardware, a processor or an integrated circuit such as a central processing unit (CPU), an application specific integrated circuit (ASIC), a field programmable gate array (FPGA) or the like. Each of the light intensity adjusting section 110, the light source control section 140, and the image processing section 150 may be formed by one CPU or the like or combination of a plurality of CPUs, ASICs, FPGAs or the like. For example, each of the pixel characteristic value calculating portion 111, the light source characteristic value calculating portion 112, and the light intensity determining portion 113 in the light intensity adjusting section 110 may include the ASIC or the like. Alternatively, for example, one CPU may function as the light intensity adjusting section 110, the light source control section 140, and the image processing section 150. The light intensity adjusting section 110, the light source control section 140, and the image processing section 150 are operated in accordance with a program stored in the storage portion 115 or a storage area in the integrated circuit. For example, the integrated circuit included in the light intensity adjusting section 110 performs various calculations to determine a light intensity of the laser light to be emitted out from the laser light source 120, resulting in that the integrated circuit functions as the light intensity adjusting section 110.

Figure 7:
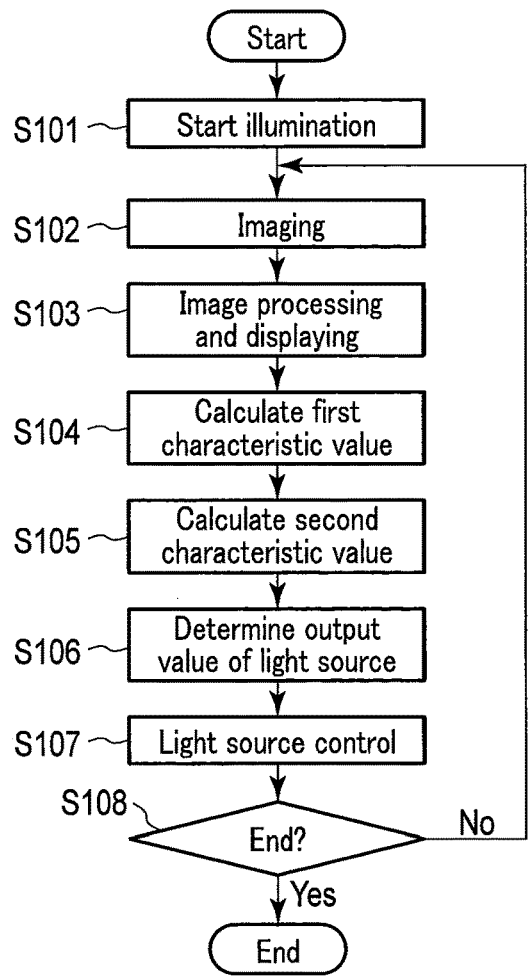
FIG. 7 is a flowchart showing one example of an operation of the observation apparatus.

Next, an operation of the observation apparatus 1 according to the present embodiment will be described with reference to a flowchart shown in FIG. 7. In step S101, the light source control section 140 controls the drive circuit 130 to drive the laser light source 120 to start illumination. At this time, an output of the laser light source 120 is defined as a predetermined initial value. In step S102, the imaging section 220 performs an imaging operation. That is, the imaging section 220 transmits, to the image processing section 150, the image data obtained in the photoelectric conversion by the image sensor 222.

In step S103, the image processing section 150 processes the image data acquired from the image sensor 222, and prepares the display data having information of the color image suitable to be displayed in the display section 160. In this case, the image processing section 150 acquires information of the output value pertaining to the light intensity of each light source in the laser light source 120 from the light intensity determining portion 113, and prepares the display data by use of this information of the output value. The image processing section 150 transmits the prepared display data to the display section 160, and the display section 160 displays the image based on the display data. Additionally, the image processing section 150 transmits the image data acquired from the imaging section 220 to the pixel characteristic value calculating portion 111 without processing the data. Here, the image data includes information on the first signal.

In step S104, the pixel characteristic value calculating portion 111 calculates the first characteristic value on the basis of the image data acquired from the image processing section 150. Here, the first characteristic value is a characteristic value pertaining to the first signal to be output by each pixel 223 included in the imaging section 220. Thus, the pixel characteristic value calculating portion 111 functions as a first characteristic value calculating portion that calculates the first characteristic value.

In the present embodiment, the first characteristic value is such a value as mentioned below. For example, all the R pixels 226 included in the image sensor 222 are referred to as an R pixel group. Similarly, for example, all the G pixels 227 included in the image sensor 222 are referred to as a G pixel group and, for example, all the B pixels 228 included in the image sensor 222 are referred to as a B pixel group. The first characteristic value includes an R pixel average intensity that is an average value of the intensities of the first signals output from the R pixel group, a G pixel average intensity that is an average value of the intensities of the first signals output from the G pixel group, and a B pixel average intensity that is an average value of the intensities of the first signals output from the B pixel group. The pixel characteristic value calculating portion 111 outputs the first characteristic value including the calculated R pixel average intensity, G pixel average intensity and B pixel average intensity to the light source characteristic value calculating portion 112.

Figure 8:
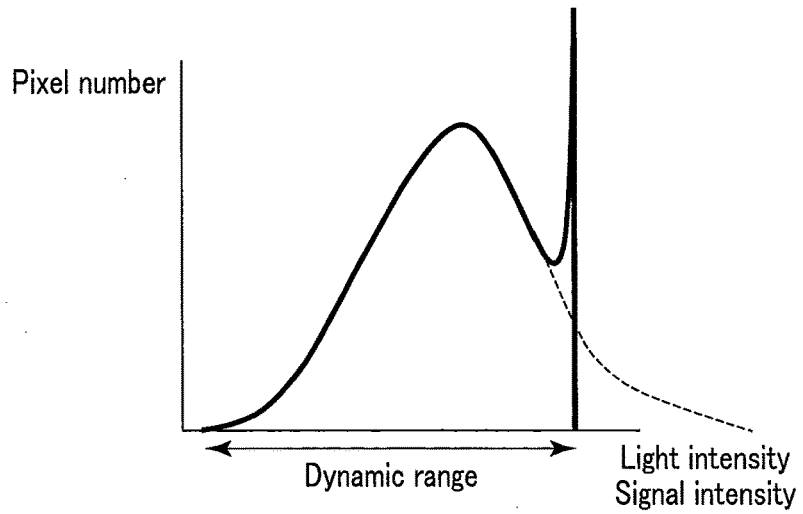
FIG. 8 is a diagram to explain a relation between light intensity of the entering light in the image sensor and its frequency, and relationship between intensity of a first signal to be generated and its frequency.

It is to be noted that the image sensor 222 has the dynamic range. For example, when a bright object in excess of the dynamic range is imaged, relations between the intensity of the entering light into each pixel of the image sensor 222 and its frequency, and relations between the intensity of the first signal to be generated and its frequency are obtained as shown in a histogram of FIG. 8. In FIG. 8, a broken line indicates a distribution of the intensity of the entering light, and a solid line shows a distribution of the signal intensities of the first signals. In such a case as shown in FIG. 8, when the average value of the intensities of the first signals is simply obtained, the value does not correctly indicate the average value of the light intensities. Therefore, not the average value but the most frequent value may be defined as the first characteristic value. In addition, when such a distribution as shown in FIG. 8 is obtained, curve fitting is performed on the basis of the histogram, and then the average value may be calculated on the basis of the fitting curve. For example, the first characteristic value is preferably set to be 0.5 times or more and 1.5 times or less as much as the simple average value of the signal intensities of the first signals. This is because a value corresponding to the average value of the intensities of the light to be received is present in a range of 0.5 times or more and 1.5 times or less as much as the simple average value.

When the intensities of the light entering into all the pixels are close to the average value, i.e., when a luminance difference of the object is small, there might not be any pixels that are overexposed or any pixels that are underexposed. In this case, the simple average value of the intensities of the first signals indicates the average value of the light intensities. However, when the average value of the light intensities is noticeably different from the average value of the dynamic range, the average value of the first signals might not indicate the average value of the light intensities. Also in this case, it is necessary to use such a calculating method as described above so that the first characteristic value is appropriately calculated.

In step S105, the light source characteristic value calculating portion 112 calculates the second characteristic value on the basis of the first characteristic value. Here, the second characteristic value is a value for each light source corresponding to the first characteristic value. Examples of the second characteristic value will be described later. The light source characteristic value calculating portion 112 outputs the second characteristic value to the light intensity determining portion 113.

In step S106, the light intensity determining portion 113 determines the output value of each light source in the laser light source 120 on the basis of the second characteristic value. The light intensity determining portion 113 transmits the determined output value of the light source to the light source control section 140 and the image processing section 150. In step S107, the light source control section 140 controls the drive circuit 130 to drive the laser light source 120 on the basis of the output value of the light source acquired from the light intensity determining portion 113.

In step S108, the light intensity determining portion 113 determines whether or not to end the illumination. For example, when a user inputs an instruction to end the illumination from an unshown input section, the illumination ends. When it is determined that the illumination does not end, the processing returns to the step S102. At this time, again in the step S102, the imaging section 220 images the object, and in the step S103, the image processing section 150 performs the image processing to prepare the display data. Here, the image processing section 150 performs the image processing on the basis of the output value of the light source determined in the step S106. That is, for example, a gain of an image signal is increased concerning the color having the low light source light intensity, and the gain of the image signal is decreased concerning the color having the high light source light intensity.

Figure 9:
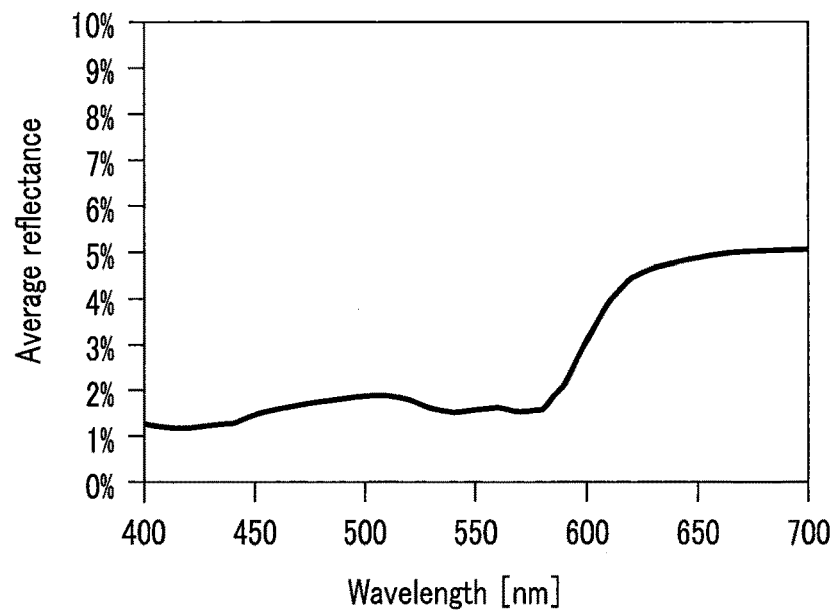
FIG. 9 is a diagram showing one example of a relation between an average reflectance of an object and a wavelength.

The abovementioned operation will further be described in an example where the object that entirely exhibits the red color is imaged. For example, there will be considered a case where the object is observed in which a relation between a wavelength and an average reflectance of the whole imaging range has such characteristics as shown in FIG. 9.

At the start of the illumination, the light intensity determining portion 113 sets each intensity of four types of laser light to be emitted out from the laser light source 120 to 100 mW. That is, in the step S101, the light intensity determining portion 113 sets the output value of each light source in the laser light source 120 to an initial value of 100 mW. At this time, the drive circuit 130 drives the laser light source 120 at an output of 100 mW.

The respective light sources, i.e., the first semiconductor laser light source 121, the second semiconductor laser light source 122, the third semiconductor laser light source 123 and the fourth semiconductor laser light source 124 emit the laser light of 100 mW. The laser light emitted out from the laser light source 120 enters into the optical coupler 180 via the optical fibers 170, and the laser light is combined by the optical coupler 180 and enters the optical fiber 215. The laser light is guided to the light emitting section 210 by the optical fiber 215, and is emitted as the illuminating light from the light emitting section 210. If a transmission efficiency of the light in the optical fibers, the optical coupler 180, the distal end optical member and the like is 50% irrespective of the wavelength, the laser light of each color is emitted out from the light emitting section 210 toward the object every 50 mW.

The object reflects the light having the spectrum corresponding to the color of the object by illumination of the illuminating light emitted out from the light emitting section 210. For example, the object having such reflection characteristics as shown in FIG. 9 is considered. At this time, when the light of each color is emitted out from the light emitting section 210 every 50 mW, the intensity of the light to be reflected by the object is as follows. That is, the light intensity of a wavelength of 440 nm is 636 μw,
the light intensity of a wavelength of 530 nm is 789 μW,
the light intensity of a wavelength of 590 nm is 1053 μW, and
the light intensity of a wavelength of 640 nm is 2368 μW.

This reflected light is transmitted through the color filter 224 of the imaging section 220 and enters the image sensor 222. According to wavelength characteristics of the color filter 224 shown in FIG. 3, the intensity of the transmitted light is as follows. That is, as to an average of the R pixels 226, the light intensity of the wavelength of 440 nm is 25 μW,
the light intensity of the wavelength of 530 nm is 47 μW, the light intensity of the wavelength of 590 nm is 937 µW, and the light intensity of the wavelength of 640 nm is 2226 µW, and the total light intensity of the respective wavelengths is 3236 µW.

As to an average of the G pixels 227,
the light intensity of the wavelength of 440 nm is 70 µW,
the light intensity of the wavelength of 530 nm is 703 µW,
the light intensity of the wavelength of 590 nm is 526 µW, and
the light intensity of the wavelength of 640 nm is 379 µW, and the total light intensity of the respective wavelengths is 1678 µW.

As to an average of the B pixels 228,
the light intensity of the wavelength of 440 nm is 572 µW,
the light intensity of the wavelength of 530 nm is 134 µW,
the light intensity of the wavelength of 590 nm is 42 µW, and
the light intensity of the wavelength of 640 nm is 166 µW, and the total light intensity of the respective wavelengths is 914 µW.

The image sensor 222 receives the entering light to perform the photoelectric conversion, and generates the image data. In the imaging section 220 according to the present embodiment, a speed variable shutter is not disposed, and the exposure time is always 10 milliseconds. The intensity of the first signal generated in the image sensor 222 that has received the light as described above is as follows on the basis of the relation shown in FIG. 4. That is, the average value of the intensities of the first signals in the R pixels 226, i.e., an R pixel average intensity is:

$$(25[\mu W] \times 231[mA/W] + 47[\mu W] \times 300[mA/W] + 937[\mu W] \times 346[mA/W] + 2226[\mu W] \times 384[mA/W]) \times 0.01 = 12.0 \ \mu A.$$

An average value of the intensities of the first signals in the G pixels 227, i.e., a G pixel average intensity is:

$$(70[\mu W] \times 231[mA/W] + 703[\mu W] \times 300[mA/W] + 526[\mu W] \times 346[mA/W] + 379[\mu W] \times 384[mA/W]) \times 0.01 = 5.5 \ \mu A.$$

An average value of the intensities of the first signals in the B pixels 228, i.e., a B pixel average intensity is:

$$(572[\mu W] \times 231[mA/W] + 134[\mu W] \times 300[mA/W] + 42[\mu W] \times 346[mA/W] + 166[\mu W] \times 384[mA/W]) \times 0.01 = 2.5 \ \mu A.$$

In the step S102, the imaging section 220 transmits the image data including the first signals to the image processing section 150. The image processing section 150 acquires the image data from the imaging section 220. In the step S103, the image processing section 150 subjects the acquired image data to the image processing to generate the display data that is the color image suitable to be displayed in the display section 160, and outputs the image data to the display section 160. In addition, the image processing section 150 transmits the image data acquired from the imaging section 220 to the pixel characteristic value calculating portion 111 of the light intensity adjusting section 110 without processing the data.

In the step S104, the pixel characteristic value calculating portion 111 calculates the first characteristic value on the basis of the image data. For example, the first characteristic value include the R pixel average intensity of 12.0 µA, the G pixel average intensity of 5.5 µA and the B pixel average intensity of 2.5 µA as described above. It is to be noted that, for example, when the average value of the dynamic range of the image sensor 222 is 5 µA, the intensity of the entering light is excessively high at the average of the R pixels, the intensity of the entering light is proper at the average of the G pixels, and the intensity of the entering light is excessively low at the average of the B pixels. The pixel characteristic value calculating portion 111 outputs the calculated first characteristic value to the light source characteristic value calculating portion 112.

In the step S105, the light source characteristic value calculating portion 112 calculates the second characteristic value that is the value pertaining to the light intensities of the four light sources in the laser light source 120 from three values, i.e., the R pixel average intensity, the G pixel average intensity and the B pixel average intensity included in the first characteristic value. Here, the second characteristic values are values indicating characteristics concerning the output correction pertaining to change of the output of each light source. Subsequently, in the step S106, the light intensity determining portion 113 determines the output of each light source in the laser light source 120. Here, there are described two methods of calculating the second characteristic value and the output value of each light source.

(First Calculating Method)

In the first calculating method, the second characteristic value calculated by the light source characteristic value calculating portion 112 is a magnification calculating value to calculate a magnification indicating the number of times as much as the present output to which the output of each light source in the laser light source 120 is to be set.

Figure 10:
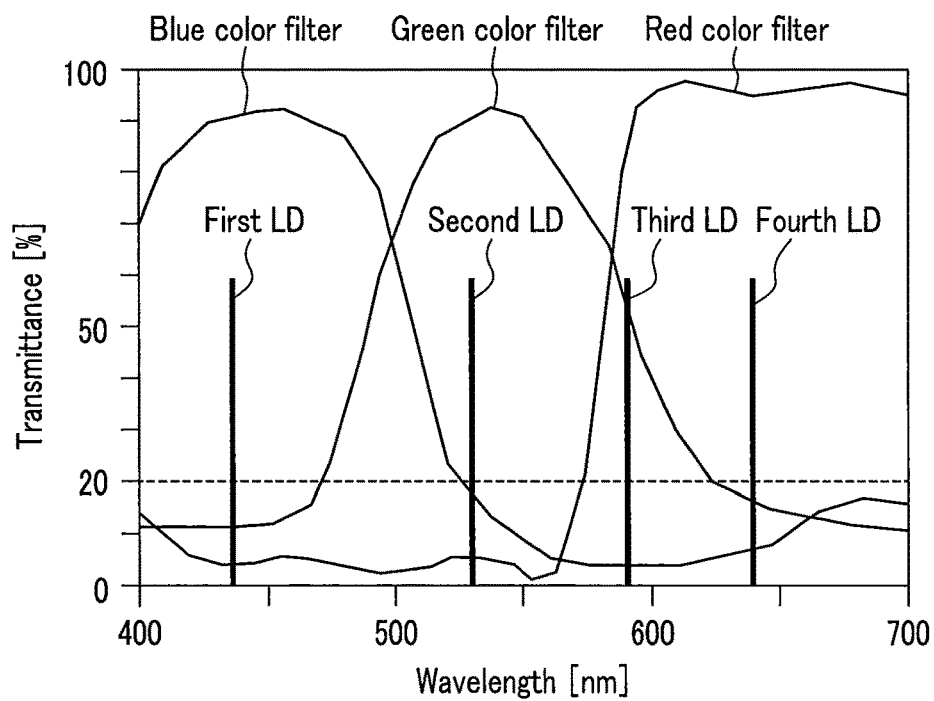
FIG. 10 is a diagram showing a relation between optical characteristics of each color filter disposed in the image sensor and a wavelength of each laser light source.

FIG. 10 shows a relation between optical characteristics of the color filter 224 disposed in the image sensor 222 and the wavelength of the laser light source. It is considered that the photoelectric conversion is performed in the image sensor 222 as to the wavelength at which the transmittance of the color filter 224 is 20% or more. At this time, the light emitted out from the first semiconductor laser light source 121 is detected only in the B pixels 228. Similarly, the light emitted out from the second semiconductor laser light source 122 is detected only in the G pixels 227, and the light emitted out from the fourth semiconductor laser light source 124 is detected only in the R pixels 226. The light emitted out from the third semiconductor laser light source 123 is detected in the G pixels 227 and the R pixels 226.

Thus, the magnification calculating value to calculate the magnification of the output of each semiconductor laser light source which is the second characteristic value is calculated in accordance with the following bases. That is, a first magnification calculating value pertaining to the first semiconductor laser light source 121 is based on the B pixel average intensity in the first characteristic value. A second magnification calculating value pertaining to the second semiconductor laser light source 122 is based on the G pixel average intensity in the first characteristic value. A third magnification calculating value pertaining to the third semiconductor laser light source 123 is based on an average value of the G pixel average intensity and the R pixel average intensity in the first characteristic value. A fourth magnification calculating value pertaining to the fourth semiconductor laser light source 124 is based on the R pixel average intensity in the first characteristic value.

In the step S105, the light source characteristic value calculating portion 112 calculates the second characteristic value including the first magnification calculating value, the second magnification calculating value, the third magnification calculating value, and the fourth magnification calculating value. The light source characteristic value calculating portion 112 transmits the calculated second characteristic value to the light intensity determining portion 113.

For example, in the abovementioned example, the light source characteristic value calculating portion 112 determines the second characteristic value as follows. That is, the first magnification calculating value pertaining to the first semiconductor laser light source 121 is 2.5. The second magnification calculating value pertaining to the second semiconductor laser light source 122 is 5.5. The third magnification calculating value pertaining to the third semiconductor laser light source 123 is (5.5+12.0)/2=8.75. The fourth magnification calculating value pertaining to the fourth semiconductor laser light source 124 is 12.0.

In the step S106, the light intensity determining portion 113 compares the reference value 116 with the second characteristic value, and calculates a correcting magnification of the output value of each light source in the laser light source. The light intensity determining portion 113 determines the following output value on the basis of the calculated correcting magnification and the present output value of each light source. On the basis of the determined output value, the drive circuit 130 is driven.

For example, when the reference value 116 is 5 µA, in the abovementioned example, a first correcting magnification pertaining to the first semiconductor laser light source 121 is calculated as:

5.0/2.5=2.0 [times].

A second correcting magnification pertaining to the second semiconductor laser light source 122 is calculated as:

5.0/5.5=0.90 [time].

A third correcting magnification pertaining to the third semiconductor laser light source 123 is calculated as:

5.0/8.75=0.57 [time].

A fourth correcting magnification pertaining to the fourth semiconductor laser light source 124 is calculated as:

5.0/12.0=0.42 [time].

On the basis of these values, the output value of the first semiconductor laser light source 121 is determined as:

100 [mW]×2.0=200 [mW].

The output value of the second semiconductor laser light source 122 is determined as:

100 [mW]×0.90=90 [mW].

The output value of the third semiconductor laser light source 123 is determined as:

100 [mW]×0.57=57 [mW].

The output value of the fourth semiconductor laser light source 124 is determined as:

100 [mW]×0.42=42 [mW].

Thus, when the output value after adjustment is L2, the output value before adjustment is L1, the reference value is S and the second characteristic value is C2, the adjusted output value L2 is represented by:

L2=L1×S/C2.

It is to be noted that the reference value may be, for example, a value of 0.5 times or more and 1.5 times or less as much as a center value of a dynamic range concerning an output signal of the image sensor.

In the step S107, an operation of the laser light source 120 is controlled on the basis of these values. When the same object is irradiated with the light of this intensity and imaged,
the R pixel average intensity is 5.7 µA,
the G pixel average intensity is 3.9 µA,
the B pixel average intensity is 3.3 µA, and
each intensity comes close to a proper intensity.

When this process is repeated three times,
the light intensity of the first semiconductor laser light source 121 is 309 mW,
the light intensity of the second semiconductor laser light source 122 is 138 mW,
the light intensity of the third semiconductor laser light source 123 is 57 mW, and
the light intensity of the fourth semiconductor laser light source 124 is 34 mW. At this time,
the R pixel average intensity is 5.1 µA,
the G pixel average intensity is 4.9 µA,
the B pixel average intensity is 4.9 µA, and
each intensity is a proper intensity close to 5 µA that is the reference value 116.

(Second Calculating Method)

A second calculating method will be described. A wavelength representing a tone of light transmitted through the color filter when standard white light is transmitted is referred to as a dominant wavelength. In the color filter 224 having optical characteristics shown in FIG. 3, a B pixel dominant wavelength that is a dominant wavelength of a blue color filter is 470 nm. Similarly, a G pixel dominant wavelength that is a dominant wavelength of a green color filter is 555 nm, and an R pixel dominant wavelength that is a dominant wavelength of a red color filter is 605 nm. As described above, when the R pixel average intensity is 12.0 µA, the G pixel average intensity is 5.5 µA and the B pixel average intensity is 2.5 µA which are the first characteristic values, FIG. 11 shows these values by use of the dominant wavelengths.

In the second calculating method, a proper light intensity of the laser light source is determined by use of a function indicating a linear relation obtained on the basis of an average signal intensity of the B pixels and an average signal intensity of the G pixels, and a function indicating a linear relation obtained on the basis of the average signal intensity of the G pixels and an average signal intensity of the R pixels. The average signal intensity of the R pixels is defined as $C_{CFR}$, the average signal intensity of the G pixels is defined as $C_{CFG}$, and the average signal intensity of the B pixels is $C_{CFB}$. The R pixel dominant wavelength is defined as $\lambda_{CFR}$, the G pixel dominant wavelength is defined as $\lambda_{CFG}$, and the B pixel dominant wavelength is defined as $\lambda_{CFB}$. At this time, an average signal intensity $C_{LS}$ to a wavelength $\lambda_{LS}$ of the laser light source is represented as follows. That is, in the function indicating the linear relation obtained on the basis of the average signal intensity of the B pixels and the average signal intensity of the G pixels, the average signal intensity is:

$$C_{LS} = (C_{CFG} - C_{CFB})/(\lambda_{CFG} - \lambda_{CFB}) \times \lambda_{LS} +$$
$$C_{CFG} - (C_{CFG} - C_{CFB})/(\lambda_{CFG} - \lambda_{CFB}) \times \lambda_{CFG}.$$

In the function indicating the linear relation obtained on the basis of the average signal intensity of the G pixels and the average signal intensity of the R pixels, the average signal intensity is:

$$C_{LS} = (C_{CFR} - C_{CFG})/(\lambda_{CFR} - \lambda_{CFG}) \times \lambda_{LS} + C_{CFR} - (C_{CFR} - C_{CFG})/(\lambda_{CFR} - \lambda_{CFG}) \times \lambda_{CFR}.$$

For example, as described above, the average signal intensity of the R pixels is 12.0 μA, the average signal intensity of the G pixels is 5.5 μA, and the average signal intensity of the B pixels is 2.5 μA. At this time, the function indicating the linear relation obtained on the basis of the average signal intensity of the B pixels and the average signal intensity of the G pixels is represented as:

$$C_{LS} = 0.036 \times \lambda_{LS} - 14.3.$$

The function indicating the linear relation obtained on the basis of the average signal intensity of the G pixels and the average signal intensity of the B pixels is represented as:

$$C_{LS} = 0.129 \times \lambda_{LS} - 66.0.$$

The light source characteristic value calculating portion 112 calculates the average signal intensity $C_{LS}$ from these linear relations and the wavelength $\lambda_{LS}$ of the laser light source as follows. That is, as to the first semiconductor laser light source 121, the average signal intensity is:

0.036×440−14.3=1.54 [μA].

As to the second semiconductor laser light source 122, the average signal intensity is:

0.036×530−14.3=4.78 [μA].

As to the third semiconductor laser light source 123, the average signal intensity is:

0.129×590−66.0=10.1 [μA].

As to the fourth semiconductor laser light source 124, the average signal intensity is:

0.129×640−66.0=16.6 [μA].

In the step S105, the light source characteristic value calculating portion 112 calculates the average signal intensity $C_{LS}$ as the second characteristic value. The second characteristic values are values indicating characteristics concerning the correction of the output of each light source. The light source characteristic value calculating portion 112 transmits the calculated second characteristic value to the light intensity determining portion 113.

The light intensity determining portion 113, by which the second characteristic value is acquired from the light source characteristic value calculating portion 112, calculates the correcting magnification of the light intensity of each laser light source from the acquired second characteristic value and the reference value 116 of, e.g., 5 μA in the step S106.

For example, in the abovementioned example, the correcting magnification pertaining to the first semiconductor laser light source 121 is calculated as:

5.0/1.54=3.5 [times].

The correcting magnification pertaining to the second semiconductor laser light source 122 is calculated as:

5.0/4.78=1.1 [times].

The correcting magnification pertaining to the third semiconductor laser light source 123 is calculated as:

5.0/10.1=0.5 [time].

The correcting magnification pertaining to the fourth semiconductor laser light source 124 is calculated as:

5.0/16.6=0.3 [time].

On the basis of these values, the light intensity of the first semiconductor laser light source 121 is determined as:

100 [mW]×3.5=350 [mW].

The light intensity of the second semiconductor laser light source 122 is determined as:

100 [mW]×1.1=110 [mW].

The light intensity of the third semiconductor laser light source 123 is determined as:

100 [mW]×0.5=50 [mW].

The light intensity of the fourth semiconductor laser light source 124 is determined as:

100 [mW]×0.3=30 [mW].

On the basis of these values, the laser light source 120 operates. When the same object is illuminated by this light intensity and imaged, the R pixel average intensity is 4.6 μA,
the G pixel average intensity is 4.2 μA, and
the B pixel average intensity is 5.3 μA.

That is, each of the values is a proper intensity close to 5 μA that is the reference value 116.

There has been described above two examples of a technique in which the light intensity determining portion 113 determines the light intensity of the laser light source 120, but any technique may be used. Additionally, in a similar spirit, another technique may be used.

The light intensity determining portion 113 further outputs the output value pertaining to the output of the laser light source 120 to the image processing section 150. The image processing section 150 subjects the image data acquired from the imaging section 220 to the image processing in consideration of the output value of the laser light source 120. That is, the image processing section 150 weights the signals acquired from the R pixels 226, the G pixels 227 and the B pixels 228 in accordance with the intensity of each corresponding laser light source 120. The image processing section 150 prepares, for example, the display data indicating the image to be displayed in the display section 160 on the basis of the weighted signal.

For example, in the abovementioned example, the intensity of the light emitted out from the first semiconductor laser light source 121 of the blue color is strong, and the intensity of the light emitted out from the fourth semiconductor laser light source 124 of the red color is weak. Therefore, the image processing section 150 further amplifies the intensity of the image signal acquired by the R pixel 226 of the imaging section 220 in accordance with the light intensity of the light source, and further decreases the intensity of the image signal acquired by the B pixel 228 in accordance with the light intensity of the light source, to prepare the display data on the basis of the intensities. Thus, the image processing section 150 performs adjustment so that the image to be displayed in the display section 160 is the image to be obtained when the object is irradiated with the white light.

It is to be noted that in the present embodiment, the light intensity of the laser light source 120 is determined so that each of the average signal intensities of the R pixels 226, the G pixels 227 and the B pixels 228 generated by the imaging section 220 which receives the light is the center of the dynamic range. However, the present invention is not limited to this example, and the average signal intensity may be adjusted to a predetermined value.

Additionally, in the present embodiment, a ratio of the light intensity of each light source is appropriately determined in accordance with the tone of the object by the abovementioned calculation. In general, during observation, a change in the object reflectance is larger than a change in the tone of the object, and the change in the object reflectance occurs due to change in an observation magnification, e.g., enlargement or reduction or change in an observation position, e.g., approaching of the imaging section 220 to the object or retreating of the imaging section from the object. Therefore, when the light intensity ratio of each light source concerning the tone is determined once, the whole light intensity may then be changed while the determined light intensity ratio is fixed as it is. That is, the light intensity adjusting section 110 may similarly change the whole light intensity of the light sources included in the laser light source 120 while the light intensity ratio of each light source included in the laser light source 120 is fixed as it is. In a situation where the tone of the object does not change much but the whole reflectance only changes, the high color reproducibility is maintained also by this method. According to this method, a calculation amount decreases.

In addition, the light intensity adjusting section 110 changes both of the light intensity concerning the change in the reflectance and the light intensity ratio of each light source concerning the tone, but may change the light intensity more often than the light intensity ratio.

In addition, when the reflectance of the object is low or a distance between the object and the light emitting section 210 is long and hence the reflected light from the object is weak, each light source is preferably driven at the maximum output. Therefore, the light intensity adjusting section 110 preferably holds information of the maximum output of the laser light source 120, and can preferably drive the laser light source 120 at the maximum output, when the output value larger than the maximum output value of the light source is calculated.

In addition, as one example when the reflected light from the object is excessively weak, there is assumed, for example, a state before the inserting part 200 is inserted into the observation object 900. Before the inserting part 200 is inserted into the observation object 900, the user can directly visually confirm the illuminating light emitted out from the light emitting section 210 without use of the imaging section 220. At this time, when the illuminating light is white, the user does not feel anything strange. Therefore, in this case, the illuminating light is preferably set to the white light.

According to the present embodiment, the intensity of the light emitted by each light source in the laser light source 120 is individually adjusted, whereby the object image of an optimum light intensity enters into the pixels of any color of the image sensor 222 in accordance with the tone of the object. Further in the image processing, the correction of the color is performed in accordance with the output value of each light source. In consequence, according to the observation apparatus 1 of the present embodiment, the high color reproducibility is realized.

Generally, in an imaging device, a shutter that controls the quantity of the light entering into the image sensor on an object side of the image sensor is disposed, or the light intensity of the whole light source is adjusted in accordance with the quantity of the light to be received by the image sensor, whereby the dynamic range of the image sensor is most broadly utilized to heighten the color reproducibility. This case is based on the assumption that the illuminating light is sunlight or the white light of an interior light or the like. That is, adjustment is not investigated in which the dynamic range is taken into consideration for each wavelength region in, e.g., a case where the object is reddish, i.e., a case where there is a deviation in the color of the object. Additionally, also in an endoscope field in which the inside of a dark view field is observed, a white color solid light source such as a xenon light source or a halogen light source is assumed as the light source, and hence the adjustment in which the dynamic range is taken into consideration for each wavelength region is not investigated.

For example, FIG. 12 shows a histogram indicating luminance values of the light entering into the R pixels, the G pixels and the B pixels when the object that exhibits the red color is imaged, and frequencies of the values. In such a case as shown in FIG. 12, when the image sensor whose dynamic range is sufficiently broad is used, the high color reproducibility can be realized. However, in general, even when a shutter speed or the quantity of the illuminating light is adjusted in any manner, a place where the red color is bright is overexposed, a place where the blue or green color is dark is underexposed, or both exposures occur, and hence the color of the object cannot exactly be reproduced. For example, in such a case as shown in FIG. 8, the image sensor cannot exactly represent the light intensity in excess of the dynamic range. Additionally, as shown in FIG. 4, there is the fear that dependency of the sensitivity of the image sensor on the wavelength also adversely affects the color reproducibility.

In the present embodiment, it is assumed that the observation apparatus 1 is used in a state where there is no other illuminating light than the light emitted out from the laser light source 120. In consequence, as described above, the light intensity of the light source of each color is individually controlled, and hence the high color reproducibility is realized. That is, the light intensity of each light source is adjusted in accordance with spectral transmission characteristics of the color filter 224 disposed in the image sensor 222, and hence the dynamic range of each pixel of the image sensor 222 is more effectively utilized as compared with a case where the intensity of the illuminating light of the white color is adjusted. In this case, information on the light source light intensity is supplied from the light intensity determining portion 113 to the image processing section 150, and hence the image processing section 150 can reproduce the color in a case where the object is illuminated with the white light. As described above, the high color reproducibility is realized.

Additionally, four wavelengths of the laser light source are selected to obtain a substantially equal interval in consideration of spectral characteristics of the color filter 224, which also produces an effect in realizing the high color reproducibility. Additionally, the dynamic range of the image sensor 222 is stored in the storage portion 115 and this value is used, or the characteristic values of the separate wavelength regions are used, which produces an effect in determining the appropriate light source light intensity. In addition, the laser light source is used as the light source, which produces an effect in emitting the bright illuminating light from the distal end of the thin inserting part.

Second Embodiment

A second embodiment will be described. Here, different points from the first embodiment are described, and the same part is denoted with the same reference signs to omit the description. In the first embodiment, the R pixel average intensity, the G pixel average intensity and the B pixel average intensity which are the first characteristic values are adjusted to obtain the average value of the dynamic range of the image sensor 222. On the other hand, in the present embodiment, intensities of light transmitted through filters of respective colors of a color filter 224 are adjusted to the same value irrespective of the color, i.e., a wavelength region. Consequently, in the present embodiment, calculation in a light source characteristic value calculating portion 112 is different from that in the first embodiment.

Also in the present embodiment, similarly to the first embodiment, it is defined that a wavelength of a first semiconductor laser light source 121 included in a laser light source 120 is 440 nm, a wavelength of a second semiconductor laser light source 122 is 530 nm, a wavelength of a third semiconductor laser light source 123 is 590 nm, and a wavelength of a fourth semiconductor laser light source 124 is 640 nm. Each of initial values of outputs of these light sources is 100 mW. There is considered a case where an object is imaged which exhibits a red color in which wavelength characteristics of reflected light have such characteristics as shown in FIG. 9. At this time, similarly to the first embodiment, first characteristic values are as follows. That is, an R pixel average intensity is 12.0 μA,
a G pixel average intensity is 5.5 μA, and
a B pixel average intensity is 2.5 μA.

The light source characteristic value calculating portion 112, by which the first characteristic values are acquired, calculates a second characteristic value pertaining to a magnification to the present output of each light source, and transmits the value to a light intensity determining portion 113. The light intensity determining portion 113 calculates an output value of the laser light source 120 on the basis of the second characteristic value. Calculations to be performed in the light source characteristic value calculating portion 112 and the light intensity determining portion 113 in the present embodiment will be described.

A dominant wavelength of a blue color filter is 470 nm, a dominant wavelength of a green color filter is 555 nm, and a dominant wavelength of a red color filter is 605 nm. In accordance with a relation between a wavelength and a sensitivity of the image sensor 222 shown in FIG. 4, a sensitivity of R pixels in the dominant wavelength is 357 mA/W,
a sensitivity of G pixels in the dominant wavelength is 319 mA/W, and
a sensitivity of B pixels in the dominant wavelength is 254 mA/W.

On the basis of the sensitivity in each dominant wavelength, an estimated value of an average value of intensities of light to be received by the respective pixels is calculated as follows. That is, an average light intensity estimated value of the R pixels is:

12.0 [μA]/357 [mA/W]/0.01=3356 [μW].

An average light intensity estimated value of the G pixels is:

5.5 [μA]/319 [mA/W]/0.01=1738 [μW].

An average light intensity estimated value of the B pixels is:

2.5 [μA]/254 [mA/W]/0.01=987 [μW].

Thus, Li1 is calculated in accordance with:

$$Li1 = C1/K_D/t,$$

in which Li1 is the average light intensity estimated value that is the estimated value of the average of the intensities of the light entering into the R pixels, the G pixels or the B pixels, C1 is the first characteristic value, $K_D$ is the sensitivity of the element in the dominant wavelength, and t is an exposure time.

A green color wavelength region is a region having the highest sensitivity for human eyes, and human eyes most precisely sense brightness or darkness in the green color wavelength region. Therefore, in the present embodiment, a proper light intensity in the green color wavelength region is defined as a reference to determine the light intensity of each wavelength region. When a reference value 116 is 5.0 μA and the sensitivity of the G pixels in the dominant wavelength is regarded as a reference, the proper light intensity is:

5.0 [μA]/319 [mA/W]/0.01=1568 [μW].

Thus, R1 is calculated in accordance with:

$$R1 = R_{center}/K_D/t,$$

in which R1 is the proper light intensity and $R_{center}$ is a reference value.

The intensities of the light entering into the respective pixels are determined so that the average light intensity estimated value of the light entering into the R pixels, the G pixels and the B pixels, respectively, is 1568 μW. That is, concerning the R pixels:

1568 [μW]/3356 [μW]=0.47 [time].

Concerning the G pixels,

1568 [μW]/1738 [μW]=0.90 [time].

Concerning the B pixels,

1568 [μW]/987 [μW]=1.6 [times].

The wavelength of the first semiconductor laser light source 121 is detected only in the B pixels, and hence an output value of the first semiconductor laser light source 121 is multiplied by 1.6. The wavelength of the second semiconductor laser light source 122 is detected only in the G pixels, and hence an output value of the second semiconductor laser light source 122 is multiplied by 0.90. The wavelength of the third semiconductor laser light source 123 is detected in the G pixels and the B pixels, and hence an output value of the third semiconductor laser light source 123 is multiplied by 1.3 that is an average value of 0.90 and 1.6. The wavelength of the fourth semiconductor laser light source 124 is detected only in the R pixels, and hence an output value of the fourth semiconductor laser light source 124 is multiplied by 0.47.

The light source characteristic value calculating portion 112 calculates the values of 1.6 times, 0.90 times, 1.3 times and 0.47 times as the second characteristic values, and transmits the values to the light intensity determining portion 113. In consequence, the second characteristic values are values indicating characteristics concerning correction of outputs of the respective light sources. The light intensity determining portion 113 determines the output value of the laser light source 120 on the basis of the second characteristic values. That is, an output of the laser light source 120 before being changed is 100 mW, and hence an output of the first semiconductor laser light source 121 is:

100 [mW]×1.6=160 [mW].

An output of the second semiconductor laser light source 122 is:

100 [mW]×0.90=90 [mW].

An output of the third semiconductor laser light source 123 is:

100 [mW]×1.3=130 [mW].

An output of the fourth semiconductor laser light source 124 is:

100 [mW]×0.47=47 [mW].

Thus, the output value of the laser light source 120 is adjusted, whereby the first characteristic values are as follows:
the R pixel average intensity is 6.4 µA,
the G pixel average intensity is 4.1 µA, and
the B pixel average intensity is 2.9 µA.
Thus, each of the R pixel average intensity, the G pixel average intensity and the B pixel average intensity comes close to 5.0 µA that is the reference value 116.

When this process is repeated three times,
the R pixel average intensity is 5.8 µA,
the G pixel average intensity is 4.8 µA,
the B pixel average intensity is 3.9 µA, and
each intensity is a proper intensity close to 5.0 µA that is the reference value 116.

According to the present embodiment, the R pixel average intensity, the G pixel average intensity and the B pixel average intensity do not match the reference value 116. However, the average value of the intensities of the light transmitted through the color filter of each color is adjusted to be a mutually equal value, and hence irrespective of a tone of the object, averages of reflected light from the object which enters pixels 223 of each color become equal to one another. For example, when the reddish object is imaged and when the bluish object is imaged, a spectrum of the reflected light from the object for an image sensor 222 has a state close to a white color. That is, the reflected light becomes light close to achromatic light so that a dynamic range is effectively utilized. Therefore, also when the image sensor is replaced with an image sensor having different light receiving characteristics by, for example, attaching and detaching an inserting part 200, high color reproducibility can be obtained irrespective of characteristics of the image sensor. According to the present modification, a system of an observation apparatus 1 does not depend on the image sensor and therefore becomes simple, so that cost reduction of the system of the observation apparatus 1 is realized.

Third Embodiment

A third embodiment will be described. Here, different points from the first embodiment are described, and the same part is denoted with the same reference signs to omit the description. In the first embodiment, the R pixel average intensity, the G pixel average intensity and the B pixel average intensity which are the first characteristic values are adjusted to obtain the average value of the dynamic range of the image sensor 222. On the other hand, in the present embodiment, table retrieval is performed on the basis of first characteristic values, and a light intensity ratio of each light source is adjusted. Here, a green color in which a sensitivity is high in human eyes is defined as a reference to determine a light intensity of each light source.

Figure 13:
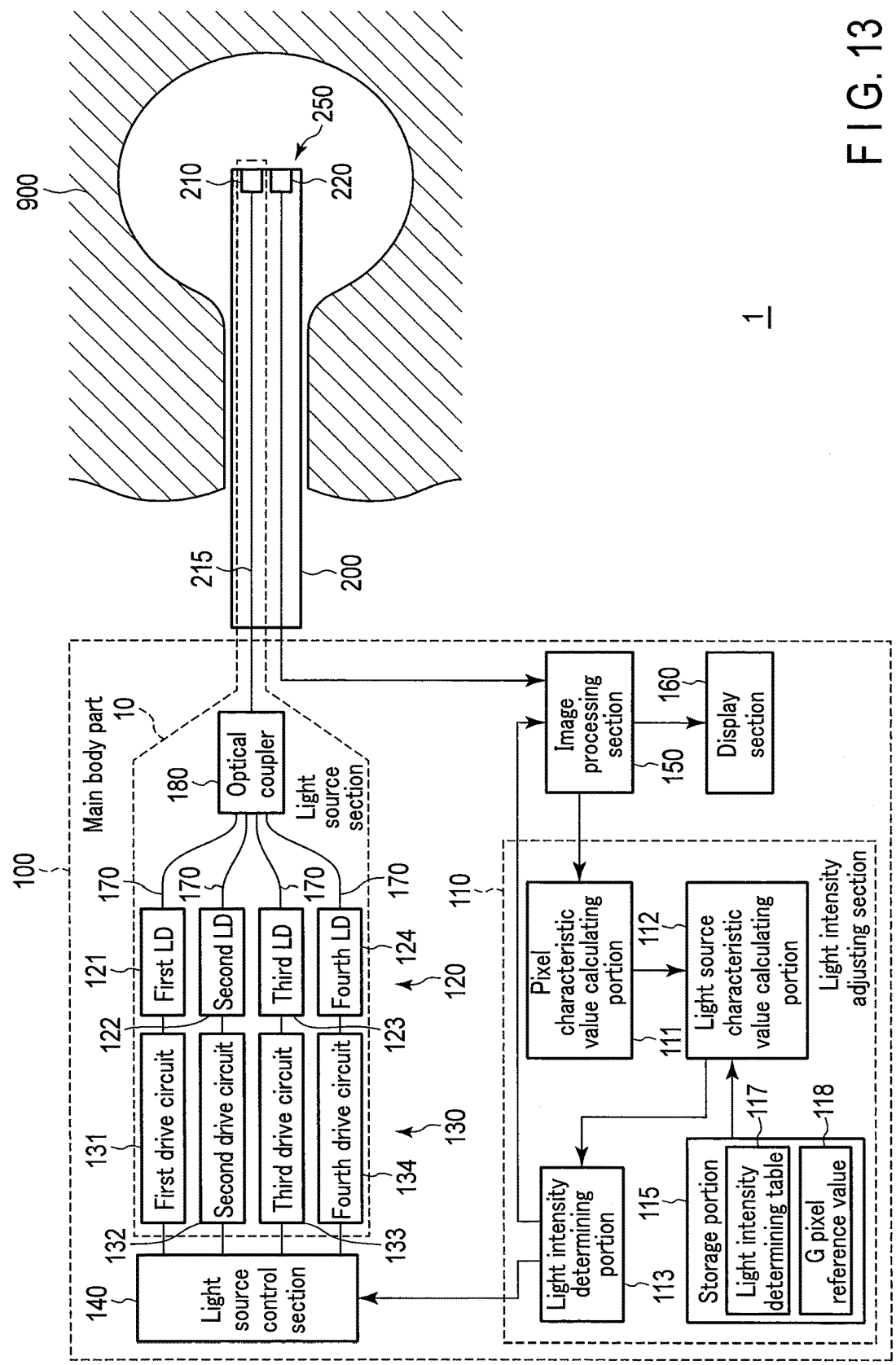
FIG. 13 is a block diagram schematically showing a configuration example of an observation apparatus according to a third embodiment.

As shown in a schematic view of FIG. 13, a light intensity determining table 117 and a G pixel reference value 118 are stored in a storage portion 115 according to the present embodiment. As shown in FIG. 14, in the light intensity determining table 117, characteristics of an object are divided into patterns for each of an R pixel average intensity/a G pixel average intensity and a B pixel average intensity/the G pixel average intensity. Here, the patterns of the object characteristics are referred to as a first assumed object, a second assumed object and the like, respectively. Furthermore, the light intensity determining table includes a reference magnification pertaining to change of an output of each light source in accordance with the patterns (the assumed objects) of the characteristics of the respective objects. In addition, the G pixel reference value 118 is a value similar to the reference value 116 of the first embodiment, and is especially a reference value of the light intensity pertaining to the G pixels.

Also in the present embodiment, similarly to the laser light source 120 of the first embodiment, it is defined that a wavelength of a first semiconductor laser light source 121 is 440 nm, a wavelength of a second semiconductor laser light source 122 is 530 nm, a wavelength of a third semiconductor laser light source 123 is 590 nm, and a wavelength of a fourth semiconductor laser light source 124 is 640 nm. Each of initial values of outputs of the respective light sources is 100 mW. There is considered a case where an object is imaged which exhibits a red color in which wavelength characteristics of reflected light have such characteristics as shown in FIG. 9.

At this time, similarly to the first embodiment, first characteristic values are as follows. That is,
an R pixel average intensity is 12.0 µA,
a G pixel average intensity is 5.5 µA, and
a B pixel average intensity is 2.5 µA.
A light source characteristic value calculating portion 112, by which the first characteristic values are acquired, calculates a second characteristic value pertaining to a magnification to the present output of each light source, and transmits the value to a light intensity determining portion 113. The light intensity determining portion 113 determines an output value of the laser light source 120 on the basis of the second characteristic value. Calculations to be performed in the light source characteristic value calculating portion 112 and the light intensity determining portion 113 in the present embodiment will be described.

The light source characteristic value calculating portion 112 calculates the R pixel average intensity and the B pixel average intensity to the G pixel average intensity, i.e., intensity ratios. For example, the R pixel average intensity/the G pixel average intensity=2.2 times, and the B pixel average intensity/the G pixel average intensity=0.45 times.

The light source characteristic value calculating portion 112 reads the light intensity determining table 117 from the storage portion 115. The light source characteristic value calculating portion 112 specifies the assumed object on the basis of the intensity ratios and the light intensity determining table 117. For example, in the case of the abovementioned example, the assumed object corresponds to the second assumed object shown in FIG. 14. The light source characteristic value calculating portion 112 acquires information corresponding to the second assumed object and indicating that a first reference value (L1) is an E time, a second reference value (L2) is an F time, a third reference value (L3) is a G time, and a fourth reference value (L4) is an H time.

The light source characteristic value calculating portion 112 determines the magnification pertaining to the change of the output of each light source using 5 µA that is the G pixel reference value 118 pertaining to a dynamic range of the G pixels and 5.5 µA that is the G pixel average intensity as follows. That is, a magnification of an output value of the first semiconductor laser light source is set to:

$$E \times 5.0/5.5 \text{ [time]},$$

a magnification of an output value of the second semiconductor laser light source is set to:

$$F \times 5.0/5.5 \text{ [time]},$$

a magnification of an output value of the third semiconductor laser light source is set to:

$$G \times 5.0/5.5 \text{ [time], and}$$

a magnification of an output value of the fourth semiconductor laser light source is set to:

$$H \times 5.0/5.5 \text{ [times]}.$$

The light source characteristic value calculating portion 112 outputs these magnifications of the output values as the second characteristic values to the light intensity determining portion 113. The light intensity determining portion 113 determines the output value of each light source included in the laser light source 120 on the basis of these magnifications of the output values, and outputs the output values to a light source control section 140.

According to the present embodiment, calculation processing in a light intensity adjusting section 110 is simplified. As a result, cost reduction of an observation apparatus 1 is realized. In addition, according to the present embodiment, when a tone does not noticeably change during observation, it is not necessary to retrieve the light intensity determining table 117, and the G pixel average intensity is only calculated, so that the laser light source 120 can be operated to appropriately utilize the dynamic range of each pixel.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
    an imager comprising elements of different types,
        wherein each of the elements of different types is configured to perform photoelectric conversion to generate a first signal when receiving light included in a sensitivity region that is a predetermined wavelength region,
        wherein the sensitivity region of the each of the elements of different types is different from one another, and
        wherein the imager is configured to generate image data including the first signal generated by the each of the elements of different types of the imager based on a color of an object image;
    a light source unit comprising light sources,
        wherein wavelengths of narrow spectrum light emitted by each of the light sources is different from one another, and
        wherein the wavelengths of the narrow spectrum light emitted by the each of the light sources are set so that at least one of the wavelengths of the narrow spectrum light is included in the sensitivity region of the each of the elements of different types of the imager; and
    a processor comprising hardware, wherein the processor is configured to:
        generate display data of a color image of based on the image data; and
        separately adjust light intensity of the narrow spectrum light emitted by the each of the light sources based at least on the color of the object image according to the first signal generated by the each of the elements of different types of the imager so that a color reproducibility of the color image heightens, by performing at least:
            calculate first characteristic values, wherein each of the first characteristic values is determined based on an intensity distribution of the first signal generated by the each of the elements of different types of the imager;
            determine the light intensity of the narrow spectrum light emitted by the each of the light sources to obtain each of the first characteristic values which makes it possible to heighten the color reproducibility of the color image;
            calculate second characteristic values, wherein each of the second characteristic values indicate a characteristic concerning output correction of the each of the light sources based on the first characteristic values;
            access a storage that stores a predetermined reference value, and
            calculate L2 in accordance with:

$$L2=L1 \times S/C2,$$

in which L1 is the light intensity of the narrow spectrum light emitted by the each of the light sources before adjustment, L2 is the light intensity of the narrow spectrum light emitted by the each of the light sources after adjustment, S is the predetermined reference value, and C2 is the each of the second characteristic values,
    wherein when the elements of same type of the imager having same sensitivity region are defined as an element group,
        the first characteristic value is a value of 0.5 times or more and 1.5 times or less as much as an average value of the first signals generated by the elements of the same type included in the element group, and
        the reference value is a value of 0.5 times or more and 1.5 times or less as much as a center value of a dynamic range concerning an output signal of the each of the elements of the same type.

2. The observation apparatus according to claim 1, wherein the processor is configured to generate the display data based on the image data and the light intensity of the narrow spectrum light emitted by the each of the light sources.

3. The observation apparatus according to claim 1, wherein at least one of the light sources of the light source unit is a laser light source.

4. The observation apparatus according to claim 1,
wherein the processor is configured to continuously adjusts the light intensity of the narrow spectrum light emitted by the each of the light sources.

5. The observation apparatus according to claim 1,
wherein wavelengths of narrow spectrum light emitted by a first light source group of the light sources of the light source unit is included only in one sensitivity region,
wherein wavelengths of narrow spectrum light emitted by a second light source group of the light sources of the light source unit is included in two or more sensitivity regions,
wherein the second characteristic value corresponding to the light sources of the first light source group is the first characteristic value pertaining to the element group having the sensitivity region including the wavelengths of the narrow spectrum light to be emitted by the light sources, and
wherein the second characteristic value corresponding to the light sources of the second light source group is an average value of two or more first characteristic values pertaining to the element group having the sensitivity region including the wavelengths of the narrow spectrum light to be emitted by the light sources.

6. An observation apparatus comprising:
an imager comprising elements of different types,
wherein each of the elements of different types is configured to perform photoelectric conversion to generate a first signal when receiving light included in a sensitivity region that is a predetermined wavelength region,
wherein the sensitivity region of the each of the elements of different types is different from one another, and
wherein the imager is configured to generate image data including the first signal generated by the each of the elements of different types of the imager based on a color of an object image;
a light source unit comprising light sources,
wherein wavelengths of narrow spectrum light emitted by each of the light sources is different from one another, and
wherein the wavelengths of the narrow spectrum light emitted by the each of the light sources are set so that at least one of the wavelengths of the narrow spectrum light is included in the sensitivity region of the each of the elements of different types of the imager; and
a processor comprising hardware, wherein the processor is configured to:
generate display data of a color image of based on the image data; and
separately adjust light intensity of the narrow spectrum light emitted by the each of the light sources based at least on the color of the object image according to the first signal generated by the each of the elements of different types of the imager so that a color reproducibility of the color image heightens, by performing at least:
calculate first characteristic values, wherein each of the first characteristic values is determined based on an intensity distribution of the first signal generated by the each of the elements of different types of the imager;
determine the light intensity of the narrow spectrum light emitted by the each of the light sources to obtain each of the first characteristic values which makes it possible to heighten the color reproducibility of the color image;
calculate second characteristic values, wherein each of the second characteristic values indicate a characteristic concerning output correction of the each of the light sources based on the first characteristic values; and
access a storage that stores a predetermined reference value,
calculate L2 in accordance with:

$$L2 = L1 \times S / C2,$$

in which L1 is the light intensity of the narrow spectrum light emitted by the each of the light sources before adjustment, L2 is the light intensity of the narrow spectrum light emitted by the each of the light sources after adjustment, S is the predetermined reference value, and C2 is the each of the second characteristic values, and
wherein the types of the elements have a dominant wavelength in each of the sensitivity regions, and $$C_{LS} = (C_{CF1} - C_{CF2})/(\lambda_{CF1} - \lambda_{CF2}) \times \lambda_{LS} + C_{CF1} - (C_{CF1} - C_{CF2})/(\lambda_{CF1} - \lambda_{CF1}) \times \lambda_{CF1},$$

in which $\lambda_{CF1}$ is the dominant wavelength closest to the wavelength of the narrow spectrum light to be emitted by the light source to be noticed, and $\lambda_{CF2}$ is the dominant wavelength second closest to the wavelength of the narrow spectrum light to be emitted by the light source to be noticed,
$C_{CF1}$ is the first characteristic value corresponding to the closest dominant wavelength,
$C_{CF2}$ is the first characteristic value corresponding to the second closest dominant wavelength,
$\lambda_{LS}$ is a wavelength of the narrow spectrum light to be emitted by the light source to be noticed, and
$C_{LS}$ is the second characteristic value concerning the light source to be noticed.

7. An observation apparatus comprising:
an imager comprising elements of different types,
wherein each of the elements of different types is configured to perform photoelectric conversion to generate a first signal when receiving light included in a sensitivity region that is a predetermined wavelength region,
wherein the sensitivity region of the each of the elements of different types is different from one another, and
wherein the imager is configured to generate image data including the first signal generated by the each of the elements of different types of the imager based on a color of an object image;
a light source unit comprising light sources,
wherein wavelengths of narrow spectrum light emitted by each of the light sources is different from one another, and
wherein the wavelengths of the narrow spectrum light emitted by the each of the light sources are set so that at least one of the wavelengths of the narrow spectrum light is included in the sensitivity region of the each of the elements of different types of the imager; and
a processor comprising hardware, wherein the processor is configured to:
generate display data of a color image based on the image data; and separately adjust light intensity of the narrow spectrum light emitted by the each of the light sources based at least on the color of the object image according to the first signal generated by the each of the elements of different types of the imager so that a color reproducibility of the color image heightens, by performing at least:

calculate first characteristic values, wherein each of the first characteristic values is determined based on an intensity distribution of the first signal generated by the each of the elements of different types of the imager;

determine the light intensity of the narrow spectrum light emitted by the each of the light sources to obtain each of the first characteristic values which makes it possible to heighten the color reproducibility of the color image;

calculate second characteristic values, wherein each of the second characteristic values indicate a characteristic concerning output correction of the each of the light sources based on the first characteristic values; and access a storage that stores a predetermined reference value, and wherein when the elements of same type of the imager having same sensitivity region are defined as an element group, the first characteristic value is a value of 0.5 times or more and 1.5 times or less as much as an average value of the first signals generated by the elements of the same type included in the element group, and Li1 is calculated in accordance with:

$$Li1 = C1/K_D/t,$$

in which Li1 is an average light intensity estimated value that is an estimated value of an average value of intensities of the light entering into the element group, C1 is the first characteristic value, $K_D$ is a sensitivity of the element in a dominant wavelength included in the sensitivity region of the element group, and t is an exposure time, the predetermined reference value is $R_{center}$ which is a value of 0.5 times or more and 1.5 times or less as much as a center value of a dynamic range concerning an output signal of the each of the elements of the same type, R1 is calculated in accordance with:

$$R1 = R_{center}/K_D/t,$$

in which R1 is a center value of a range of intensity of light to be received which is exactly photoelectrically convertible by the element included in the element group, wherein the processor is configured to:
calculate the each of the second characteristic values based on R1/Li1; and
individually adjusts the light intensity of the narrow spectrum light emitted by the each of the light sources based on the each of the second characteristic values calculated.

8. The observation apparatus according to claim 7, wherein wavelengths of narrow spectrum light emitted by a first light source group of the light sources of the light source unit is included only in one sensitivity region, wherein wavelengths of narrow spectrum light emitted by a second light source group of the light sources of the light source unit is included in two or more sensitivity regions, wherein the second characteristic value corresponding to the light sources of the first light source group is the R1/Li1 pertaining to the element having the sensitivity region including the wavelength of the narrow spectrum light to be emitted by the light source, and wherein the second characteristic value corresponding to the light sources of the second light source group is an average value of two or more R1/Li1 values pertaining to the element having the sensitivity region including the wavelength of the narrow spectrum light to be emitted by the light source.

9. An observation apparatus comprising:
an imager comprising elements of different types,
wherein each of the elements of different types is configured to perform photoelectric conversion to generate a first signal when receiving light included in a sensitivity region that is a predetermined wavelength region,
wherein the sensitivity region of the each of the elements of different types is different from one another, and
wherein the imager is configured to generate image data including the first signal generated by the each of the elements of different types of the imager based on a color of an object image;

a light source unit comprising light sources,
wherein wavelengths of narrow spectrum light emitted by each of the light sources is different from one another, and
wherein the wavelengths of the narrow spectrum light emitted by the each of the light sources are set so that at least one of the wavelengths of the narrow spectrum light is included in the sensitivity region of the each of the elements of different types of the imager; and a processor comprising hardware, wherein the processor is configured to:
generate display data of a color image based on the image data; and
separately adjust light intensity of the narrow spectrum light emitted by the each of the light sources based at least on the color of the object image according to the first signal generated by the each of the elements of different types of the imager so that a color reproducibility of the color image heightens, by performing at least:

calculate first characteristic values, wherein each of the first characteristic values is determined based on an intensity distribution of the first signal generated by the each of the elements of different types of the imager;

determine the light intensity of the narrow spectrum light emitted by the each of the light sources to obtain each of the first characteristic values which makes it possible to heighten the color reproducibility of the color image;

continuously adjust the light intensity of the narrow spectrum light emitted by the each of the light sources;

perform a light intensity ratio changing operation of changing a light intensity ratio between the light sources; and perform a whole light intensity changing operation of uniformly changing the light intensity of all the light sources without changing the light intensity ratio between the light sources, wherein a frequency of the whole light intensity changing operation is higher than a frequency of the light intensity ratio changing operation.

10. The observation apparatus according to claim 9, wherein when the each of the first characteristic values is a predetermined value or less, the processor is configured to determine the light intensity of the narrow spectrum light emitted by the each of the light sources as an upper limit.

11. The observation apparatus according to claim 10, wherein when the light intensity of the narrow spectrum light emitted by all the light sources is the upper limit, mixed light of the narrow spectrum light to be emitted is white.

12. The observation apparatus according to claim 9, wherein a wavelength number of the narrow spectrum light to be emitted by the light source unit is 4 or more.

* * * * *